(12) United States Patent
Qin et al.

(10) Patent No.: US 12,331,045 B2
(45) Date of Patent: Jun. 17, 2025

(54) SUBSTITUTED PHENYL OXAZOLONE COMPOUNDS

(71) Applicant: Bristol-Myers Squibb Company, Princeton, NJ (US)

(72) Inventors: Lan-Ying Qin, Plainsboro, NJ (US); Zheming Ruan, Dayton, NJ (US); Ashok Vinayak Purandare, Pennington, NJ (US); Emily Charlotte Cherney, Newtown, PA (US); James Aaron Balog, Lambertville, NJ (US); Arvind Mathur, Bridgewater, NJ (US); Samuel J. Bonacorsi, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 18/968,101

(22) Filed: Dec. 4, 2024

(65) Prior Publication Data

US 2025/0129061 A1 Apr. 24, 2025

Related U.S. Application Data

(63) Continuation of application No. PCT/US2024/028082, filed on May 7, 2024.

(60) Provisional application No. 63/632,070, filed on Apr. 10, 2024, provisional application No. 63/500,727, filed on May 8, 2023.

(51) Int. Cl.
| | | |
|---|---|---|
| C07D 413/14 | (2006.01) | |
| A61K 31/4545 | (2006.01) | |
| A61K 45/06 | (2006.01) | |
| C07B 59/00 | (2006.01) | |

(52) U.S. Cl.
CPC ........ *C07D 413/14* (2013.01); *A61K 31/4545* (2013.01); *A61K 45/06* (2013.01); *C07B 59/002* (2013.01)

(58) Field of Classification Search
CPC .............. C07D 413/14; A61K 31/4545; A61K 45/06; C07B 59/002
See application file for complete search history.

(56) References Cited

FOREIGN PATENT DOCUMENTS

| WO | 2014116573 A1 | 7/2014 |
|---|---|---|
| WO | 2019060693 A1 | 3/2019 |
| WO | 2019133531 A1 | 7/2019 |
| WO | 2020113233 A1 | 6/2020 |

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Bianchi et al. (Current Opinion in Cell Biology. 2020; 63:135-143) (Year: 2020).*
Akimova, et al., "Helios Expression Is a Marker of T Cell Activation and Proliferation", PLoS One, 2011, vol. 6, Iss. 8, e24226.
Antony, et al., "CD8+ T Cell Immunity Against a Tumor/Self-Antigen Is Augmented by CD4+ T Helper Cells and Hindered by Naturally Occurring T Regulatory Cells" J Immunol 174(5) 2591-2602 (2005).
Bandyopadhyay, et al., "Interleukin 2 gene transcription is regulated by Ikaros-induced changes in histone acetylation in anergic T cells", Blood, 2007, vol. 109, No. 7, 2878.
Bonazzi, et al., "Discovery and characterization of a selective IKZF2glue degrader for cancer immunotherapy", Cell Chemical Biology, 2023, vol. 30, 235-247.
Bos, et al., "Transient regulatory T cell ablation deters oncogene-driven breast cancer and enhances radiotherapy", J. Exp. Med. 2013 vol. 210 No. 11 2435-2446.
Brown, et al., "Association of Transcriptionally Silent Genes with Ikaros Complexes at Centromeric Heterochromatin", Cell, 1997, vol. 91, 845-854.
Chen, et al., "Oncology Meets Immunology: The Cancer-Immunity Cycle", Immunity 39, 2013, 1-10.
Cooney, et al., "Phase I trial of pomalidomide given for patients with advanced solid tumors", Cancer Chemother Pharmacol (2012) 70:755-761.
Dias, et al., "Multiple layers of heterogeneity and subset diversity inhuman MAIT cell responses to distinct microorganisms and to innate cytokines", PNAS, 2017, E5434-E5443.
Dsouza, et al., "Understanding the Role of T-Cells in the Antimyeloma Effect of Immunomodulatory Drugs", Frontiers in Immunology, 2021, vol. 12, Article 632399, 1-8.

(Continued)

*Primary Examiner* — Brandon J Fetterolf
*Assistant Examiner* — Jerica Katlynn Wilson
(74) *Attorney, Agent, or Firm* — Gary Greenblatt

(57) ABSTRACT

Disclosed are compounds of Formula (I):

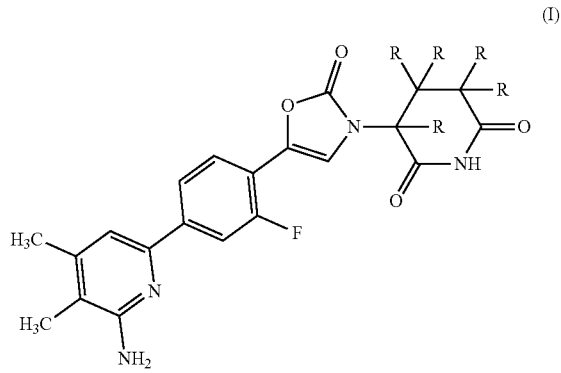

or stereoisomers, tautomers, or salts thereof, wherein each R is independently H or D. Also disclosed are methods of using such compounds to decrease the levels of IKZF1-4 proteins; and pharmaceutical compositions comprising the compound. The compounds are useful in the treatment of viral infections and proliferative disorders, such as cancer.

27 Claims, No Drawings

Specification includes a Sequence Listing.

(56) References Cited

OTHER PUBLICATIONS

Fu, et al., "A multiply redundant genetic switch 'locks in' the transcriptional signature of regulatory T cells", Nature Immunology, 2012, vol. 13, No. 10, 972-982.
Galustian, et al., "The anti-cancer agents lenalidomide and pomalidomide inhibit the proliferation and function of T regulatory cells", Cancer Immunol Immunother, 2009, 58:1033-1045.
Gandhi, et al., "Activation of the aryl hydrocarbon receptor induces human type 1 regulatory T cell-like and Foxp3+ regulatory T cells", Nature Immunology, 2010, vol. 11, No. 9, 846-854.
Geng, et al., "Lenalidomide bypasses CD28 co-stimulation to reinstate PD-1 immunotherapy by activating Notch signaling", Cell Chemical Biology, 2022, 29, 1260-1272.
Georgopoulos, et al., "The making of a lymphocyte: the choiceamong disparate cell fates and the IKAROS enigma", 2017, Genes & Development 31:439-450.
Gokhale, et al., Selective deletion of Eos (Ikzf4) in T-regulatory cells leads to loss of suppressive function and development of systemic autoimmunity, Journal of Autoimmunity, 20'19, 105, 102300.
Heizmann, et al., "The Ikaros family in lymphocyte development", Current Opinion in Immunology 2018, 51:14-23.
Heller, et al., "Restriction of IL-22-Producing T Cell Responses and Diyerential Regulation of Regulatory T Cell Compartments by Zinc Finger Transcription Factor Ikaros", J Immunol, 2014, 193 (8): 3934-3946.
Hetemaki, et al., "Loss-of-function mutation in IKZF2 leads to immunodeficiency with dysregulated germinal center reactions and reduction of MAIT cells", Sci. Immunol., 2021, 6, eabe3454.
Hideshima, et al., "Immunomodulatory drugs activate NK cells via both Zap-70 and cereblon-dependent pathways", Leukemia, 2021, 35:177-188.
International Search Report for PCT Application PCT/US2024/028082, mailed Oct. 2, 2024.
Kim, et al., "Stable inhibitory activity of regulatory T cells requires thetranscription factor Helios", Science, vol. 350 Issue 6258, 334-339.
Koipally, et al., "A Molecular Dissection of the Repression Circuitry of Ikaros", The Journal of Biological Chemistry, 2002, vol. 277, No. 31, Issue of August 2, pp. 27697-27705.
LYON_de_Ana, et al., "Lack of Ikaros Deregulates Inflammatory Gene Programs in T Cells", J Immunol (2019) 202 (4): 1112-1123.
Nakagawa, et al., "Instability of Helios-deficient Tregs is associated with coversion to a T-effector phenotype and enhanced antitumor immunity" PNAS 113(22) 6248-6253 (2016).
Nishikawa, et al., "Regulatory T cells in tumor immunity" Int J Cancer 127, 759-767 (2010).
Obrien, et al., "Ikaros Imposes a Barrier to CD8+ T Cell Diyerentiation by Restricting Autocrine IL-2 Production", J Immunol, 2014, 192 (11): 5118-5129.
Pan, et al., "Eos Mediates Foxp3-Dependent Gene Silencing in CD4+ Regulatory T Cells", Science, 2009, vol. 325, 1142-1146.
Plitas, et al., "Regulatory T Cells in Cancer", Annu. Rev. Cancer Biol. 2020, 4:459-77.
Powell, et al., "Ikaros Zinc Finger Transcription Factors: Regulators of Cytokine Signaling Pathways and CD4+ T Helper Cell Differentiation", Frontiers in Immunology, 2019, vol. 10, Article 1299, 1-11.
Punkosdy, et al., "Regulatory T-cell expansion during chronic viral infection is dependent on endogenous retroviral superantigens" PNAS 108 3677-3682 (2011).
Quintana, et al., "Aiolos promotes TH17 differentiation by directlysilencing Il2 expression", Nature Immunology, vol. 13, No. 8, 770-779.
Rasco, et al., "A First-in-Human Study of Novel Cereblon Modulator Avadomide (CC-122) in Advanced Malignancies", Clin Cancer Res, 2019, 25(1), 90-98.

Read, et al., "Established and emergent roles for Ikaros transcription factors in lymphoid cell development and function", Immunological Reviews, 2021;300:82-99.
Read, et al., "Integrated STAT3 and Ikaros Zinc Finger Transcription Factor Activities Regulate Bcl-6 Expression in CD4+ Th Cells", J Immunol, 2017, 199 (7): 2377-2387.
Rieder, et al., "Eos Is Redundant for Regulatory T Cell Function but Plays an Important Role in IL-2 and Th17 Production by CD4+ Conventional T Cells", J Immunol, 2015, 195 (2): 553-563.
Russak, et al., "Impact of Deuterium Substitution on the Pharmacokinetics of Pharmaceuticals", Annals of Pharmacotherapy, 2018, 1-6.
Sakaguchi, et al., "Regulatory T Cells and Human Disease", Annu. Rev. Immunol, 2020, 38:541-66.
Schmitz, et al., "IL-21 Restricts Virus-driven Treg Cell Expansion in Chronic LCMV Infection" PLOS Pathogens 9 e1003362 (2013).
Sebastian, et al., "Helios Controls a Limited Subset of Regulatory T Cell Functions" J Immunol 196 144-155 (2016).
Semeraro, et al., "Trial Watch: Lenalidomide-based immunochemotherapy", OncoImmunology, 2013, 2:11, e26494, 1-16.
Shahin, et al., "Germline biallelic mutation affecting the transcriptionfactor Helios causes pleiotropic defects of immunity", Sci. Immunol, 2021, 6, eabe3981.
Shang, et al., "Prognostic value of tumorinfiltratingFoxP3+ regulatory T cells in cancers: a systematic review and meta-analysis", Scientific Reports, 2015, 5:15179, 1-9.
Sharma, et al., "An Inherently Bifunctional Subset of Foxp3+ T Helper Cells Is Controlled by the Transcription Factor Eos", Immunity, 2013, 38, 998-1012.
Takahashi, et al., "Immunologic self-tolerance maintained by CD25+ CD4+ naturally anergic and suppresive T cells: induction of autoimmune disease by breaking their anergic/suppresive state" Int Immuno 10 1969-1980 (1998).
Tanaka, et al., "Targeting Treg cells in cancer immunotherapy", Eur.]. Immunol, 2019, 49: 1140-1146.
Tanaka, et al., "Regulatory T cells in cancer immunotherapy" Cell Research 27 109-118 (2017).
Thomas, et al., "Ikaros Enforces the Costimulatory Requirement for IL2 Gene Expression and Is Required for Anergy Induction in CD4+ T Lymphocytes", J Immunol, 2007, 179 (11): 7305-7315.
Thompson, et al., "Ikaros DNA-Binding Proteins as Integral Components of B Cell Developmental-Stage-Specific Regulatory Circuits", Immunity, 2007, 26, 335-344.
Thornton et al., "CD4+CD25+ Immunoregulatory T Cells Suppress Polyclonal T Cell Activation In Vitro by Inhibiting Interleukin 2 Production" J Experimental Medicine 188(2) 287-296 (1998).
Thornton, et al., "Helios: still behind the clouds", Immunology, 158, 161-170.
Wang, et al., "Comparison of Survival Between Autologous and Allogeneic Stem Cell Transplantation in Patients with Relapsed or Refractory B-Cell Non-Hodgkin Lymphoma: A Meta-Analysis", Cell Transplantation, 2020, vol. 29: 1-15.
Whibley, et al., "Regulatory T cell adaptation in the intestine and skin", Nature Immunology, 2019, 386, vol. 20, 386-396.
Wu, et al., "Stromal PD-L1-Positive Regulatory T cells and PD-1-Positive CD8-Positive T cells Define the Response of Different Subsets of Non-Small Cell Lung Cancer to PD-1/PD-L1 Blockade Immunotherapy", Journal of Thoracic Oncology, 2017, vol. 13 No. 4: 521-532.
Yates, et al., "Comparative transcriptome analysis reveals distinct genetic modules associated with Helios expression in intratumoral regulatory T cells" PNAS 115 2162-2167 (2018).
Yu et al., "Intratumor depletion of CD4+ cells unmasks tumor immunogenicity leading to the rejection of late-stage tumors" J. Experimental Medicine, vol. 201(5) 779-791 (2005).
Zhang, et al., "Harnessing of the nucleosome-remodeling-deacetylase complex controls lymphocyte development and prevents leukemogenesis", Nature Immunology, 2012, vol. 13, No. 1, 86-95.

* cited by examiner

SEQUENCE LISTING

```
Sequence total quantity: 25
SEQ ID NO: 1                  moltype = AA  length = 519
FEATURE                       Location/Qualifiers
source                        1..519
                              mol_type = protein
                              organism = Homo sapiens
SEQUENCE: 1
MDADEGQDMS QVSGKESPPV SDTPDEGDEP MPIPEDLSTT SGGQQSSKSD RVVASNVKVE  60
TQSDEENGRA CEMNGEECAE DLRMLDASGE KMNGSHRDQG SSALSGVGGI RLPNGKLKCD  120
ICGIICIGPN VLMVHKRSHT GERPFQCNQC GASFTQKGNL LRHIKLHSGE KPFKCHLCNY  180
ACRRRDALTG HLRTHSVGKP HKCGYCGRSY KQRSSLEEHK ERCHNYLESM GLPGTLYPVI  240
KEETNHSEMA EDLCKIGSER SLVLDRLASN VAKRKSSMPQ KFLGDKGLSD TPYDSSASYE  300
KENEMMKSHV MDQAINNAIN YLGAESLRPL VQTPPGGSEV VPVISPMYQL HKPLAEGTPR  360
SNHSAQDSAV ENLLLLSKAK LVPSEREASP SNSCQDSTDT ESNNEEQRSG LIYLTNHIAP  420
HARNGLSLKE EHRAYDLLRA ASENSQDALR VVSTSGEQMK VYKCEHCRVL FLDHVMYTIH  480
MGCHGFRDPF ECNMCGYHSQ DRYEFSSHIT RGEHRFHMS                        519

SEQ ID NO: 2                  moltype = AA  length = 432
FEATURE                       Location/Qualifiers
source                        1..432
                              mol_type = protein
                              organism = Homo sapiens
SEQUENCE: 2
MDADEGQDMS QVSGKESPPV SDTPDEGDEP MPIPEDLSTT SGGQQSSKSD RVVGERPFQC  60
NQCGASFTQK GNLLRHIKLH SGEKPFKCHL CNYACRRRDA LTGHLRTHSV GKPHKCGYCG  120
RSYKQRSSLE EHKERCHNYL ESMGLPGTLY PVIKEETNHS EMAEDLCKIG SERSLVLDRL  180
ASNVAKRKSS MPQKFLGDKG LSDTPYDSSA SYEKENEMMK SHVMDQAINN AINYLGAESL  240
RPLVQTPPGG SEVVPVISPM YQLHKPLAEG TPRSNHSAQD SAVENLLLLS KAKLVPSERE  300
ASPSNSCQDS TDTESNNEEQ RSGLIYLTNH IAPHARNGLS LKEEHRAYDL LRAASENSQD  360
ALRVVSTSGE QMKVYKCEHC RVLFLDHVMY TIHMGCHGFR DPFECNMCGY HSQDRYEFSS  420
HITRGEHRFH MS                                                     432

SEQ ID NO: 3                  moltype = AA  length = 432
FEATURE                       Location/Qualifiers
source                        1..432
                              mol_type = protein
                              organism = Homo sapiens
SEQUENCE: 3
MDADEGQDMS QVSGKESPPV SDTPDEGDEP MPIPEDLSTT SGGQQSSKSD RVVASNVKVE  60
TQSDEENGRA CEMNGEECAE DLRMLDASGE KMNGSHRDQG SSALSGVGGI RLPNGKLKCD  120
ICGIICIGPN VLMVHKRSHT GERPFQCNQC GASFTQKGNL LRHIKLHSGE KPFKCHLCNY  180
ACRRRDALTG HLRTHSGDKG LSDTPYDSSA SYEKENEMMK SHVMDQAINN AINYLGAESL  240
RPLVQTPPGG SEVVPVISPM YQLHKPLAEG TPRSNHSAQD SAVENLLLLS KAKLVPSERE  300
ASPSNSCQDS TDTESNNEEQ RSGLIYLTNH IAPHARNGLS LKEEHRAYDL LRAASENSQD  360
ALRVVSTSGE QMKVYKCEHC RVLFLDHVMY TIHMGCHGFR DPFECNMCGY HSQDRYEFSS  420
HITRGEHRFH MS                                                     432

SEQ ID NO: 4                  moltype = AA  length = 388
FEATURE                       Location/Qualifiers
source                        1..388
                              mol_type = protein
                              organism = Homo sapiens
SEQUENCE: 4
MDADEGQDMA SNVKVETQSD EENGRACEMN GEECAEDLRM LDASGEKMNG SHRDQGSSAL  60
SGVGGIRLPN GKLKCDICGI ICIGPNVLMV HKRSHTGERP FQCNQCGASF TQKGNLLRHI  120
KLHSGEKPFK CHLCNYACRR RDALTGHLRT HSGDKGLSDT PYDSSASYEK ENEMMKSHVM  180
DQAINNAINY LGAESLRPLV QTPPGGSEVV PVISPMYQLH KPLAEGTPRS NHSAQDSAVE  240
NLLLLSKAKL VPSEREASPS NSCQDSTDTE SNNEEQRSGL IYLTNHIAPH ARNGLSLKEE  300
HRAYDLLRAA SENSQDALRV VSTSGEQMKV YKCEHCRVLF LDHVMYTIHM GCHGFRDPFE  360
CNMCGYHSQD RYEFSSHITR GEHRFHMS                                    388

SEQ ID NO: 5                  moltype = AA  length = 477
FEATURE                       Location/Qualifiers
source                        1..477
                              mol_type = protein
                              organism = Homo sapiens
SEQUENCE: 5
MDADEGQDMS QVSGKESPPV SDTPDEGDEP MPIPEDLSTT SGGQQSSKSD RVVASNVKVE  60
TQSDEENGRA CEMNGEECAE DLRMLDASGE KMNGSHRDQG SSALSGVGGI RLPNGKLKCD  120
ICGIICIGPN VLMVHKRSHT GERPFQCNQC GASFTQKGNL LRHIKLHSGE KPFKCHLCNY  180
ACRRRDALTG HLRTHSVIKE ETNHSEMAED LCKIGSERSL VLDRLASNVA KRKSSMPQKF  240
LGDKGLSDTP YDSSASYEKE NEMMKSHVMD QAINNAINYL GAESLRPLVQ TPPGGSEVVP  300
VISPMYQLHK PLAEGTPRSN HSAQDSAVEN LLLLSKAKLV PSEREASPSN SCQDSTDTES  360
```

```
NNEEQRSGLI YLTNHIAPHA RNGLSLKEEH RAYDLLRAAS ENSQDALRVV STSGEQMKVY    420
KCEHCRVLFL DHVMYTIHMG CHGFRDPFEC NMCGYHSQDR YEFSSHITRG EHRFHMS       477

SEQ ID NO: 6           moltype = AA  length = 226
FEATURE                Location/Qualifiers
source                 1..226
                       mol_type = protein
                       organism = Homo sapiens
SEQUENCE: 6
MDADEGQDMS QVSGKESPPV SDTPDEGDEP MPIPEDLSTT SGGQQSSKSD RVVASNVKVE    60
TQSDEENGRA CEMNGEECAE DLRMLDASGE KMNGSHRDQG SSALSGVGGI RLPNGKLKCD    120
ICGIICIGPN VLMVHKRSHT GERPFQCNQC GASFTQKGNL LRHIKLHSGE KPFKCHLCNY    180
ACRRRDALTG HLRTHSVIKE ETNHSEMAED LCKIGSEISR AGQTSK                   226

SEQ ID NO: 7           moltype = AA  length = 525
FEATURE                Location/Qualifiers
source                 1..525
                       mol_type = protein
                       organism = Homo sapiens
SEQUENCE: 7
METEAIDGYI TCDNELSPER EHSNMAIDLT SSTPNGQHAS PSHMTSTNSV KLEMQSDEEC    60
DRKPLSREDE IRGHDEGSSL EEPLIESSEV ADNRKVQELQ GEGGIRLPNG KLKCDVCGMV    120
CIGPNVLMVH KRSHTGERPF HCNQCGASFT QKGNLLRHIK LHSGEKPFKC PFCSYACRRR    180
DALTGHLRTH SVGKPHKCNY CGRSYKQRSS LEEHKERCHN YLQNVSMEAA GQVMSHHVPP    240
MEDCKEQEPI MDNNISLVPF ERPAVIEKLT GNMGKRKSST PQKFVGEKLM RFSYPDIHFD    300
MNLTYEKEAE LMQSHMMDQA INNAITYLGA EALHPLMQHP PSTIAEVAPV ISSAYSQVYH    360
PNRIERPISR ETADSHENNM DGPISLIRPK SRPQEREASP SNSCLDSTDS ESSHDDHQSY    420
QGHPALNPKR KQSPAYMKED VKALDTTKAP KGSLKDIYKV FNGEGEQIRA FKCEHCRVLF    480
LDHMYTIHMG CHGYRDPLEC NICGYRSQDR YEFSSHIVRG EHTFH                    525

SEQ ID NO: 8           moltype = AA  length = 500
FEATURE                Location/Qualifiers
source                 1..500
                       mol_type = protein
                       organism = Homo sapiens
SEQUENCE: 8
METEAIDGYI TCDNELSPER EHSNMAIDLT SSTPNGQHAS PSHMTSTNSV KLEMQSDEEC    60
DRKPLSREDE IRGHDEGSSL EEPLIESSEV ADNRKVQELQ GEGGIRLPNG ERPFHCNQCG    120
ASFTQKGNLL RHIKLHSGEK PFKCPFCSYA CRRRDALTGH LRTHSVGKPH KCNYCGRSYK    180
QRSSLEEHKE RCHNYLQNVS MEAAGQVMSH HVPPMEDCKE QEPIMDNNIS LVPFERPAVI    240
EKLTGNMGKR KSSTPQKFVG EKLMRFSYPD IHFDMNLTYE KEAELMQSHM MDQAINNAIT    300
YLGAEALHPL MQHPPSTIAE VAPVISSAYS QVYHPNRIER PISRETADSH ENNMDGPISL    360
IRPKSRPQER EASPSNSCLD STDSESSHDD HQSYQGHPAL NPKRKQSPAY MKEDVKALDT    420
TKAPKGSLKD IYKVFNGEGE QIRAFKCEHC RVLFLDHTMY TIHMGCHGYR DPLECNICGY    480
RSQDRYEFSS HIVRGEHTFH                                                500

SEQ ID NO: 9           moltype = AA  length = 451
FEATURE                Location/Qualifiers
source                 1..451
                       mol_type = protein
                       organism = Homo sapiens
SEQUENCE: 9
METEAIDGYI TCDNELSPER EHSNMAIDLT SSTPNGQHAS PSHMTSTNSV KLEMQSDEEC    60
DRKPLSREDE IRGHDEGSSL EEPLIESSEV ADNRKVQELQ GEGGIRLPNG ERPFHCNQCG    120
ASFTQKGNLL RHIKLHSGEK PFKCPFCSYA CRRRDALTGH LRTHSVGKPH KCNYCGRSYK    180
QRSSLEEHKE RCHNYLQNVS MEAAGQVMSH HGEKLMRFSY PDIHFDMNLT YEKEAELMQS    240
HMMDQAINNA ITYLGAEALH PLMQHPPSTI AEVAPVISSA YSQVYHPNRI ERPISRETAD    300
SHENNMDGPI SLIRPKSRPQ EREASPSNSC LDSTDSESSH DDHQSYQGHP ALNPKRKQSP    360
AYMKEDVKAL DTTKAPKGSL KDIYKVFNGE GEQRAFKCEH CRVLFLDHVM YTIHMGCHGY    420
RDPLECNICG YRSQDRYEFS SHIVRGEHTF H                                   451

SEQ ID NO: 10          moltype = AA  length = 239
FEATURE                Location/Qualifiers
source                 1..239
                       mol_type = protein
                       organism = Homo sapiens
SEQUENCE: 10
METEAIDGYI TCDNELSPER EHSNMAIDLT SSTPNGQHAS PSHMTSTNSV KLEMQSDEEC    60
DRKPLSREDE IRGHDEGSSL EEPLIESSEV ADNRKVQELQ GEGGIRLPNG KLKCDVCGMV    120
CIGPNVLMVH KRSHTGERPF HCNQCGASFT QKGNLLRHIK LHSGEKPFKC PFCSYACRRR    180
DALTGHLRTH SVGKPHKCNY CGRSYKQRSS LEEHKERCHN YLQNVSMEAA GQVMSHHDS     239
```

```
SEQ ID NO: 11              moltype = AA  length = 454
FEATURE                    Location/Qualifiers
source                     1..454
                           mol_type = protein
                           organism = Homo sapiens
SEQUENCE: 11
METEAIDGYI TCDNELSPER EHSNMAIDLT SSTPNGQHAS PSHMTSTNSV KLEMQSDEEC    60
DRKPLSREDE IRGHDEGSSL EEPLIESSEV ADNRKVQELQ GEGGIRLPNG ERPFHCNQCG   120
ASFTQKGNLL RHIKLHSGEK PFKCPFCSYA CRRRDALTGH LRTHSVPPME DCKEQEPIMD   180
NNISLVPFER PAVIEKLTGN MGKRKSSTPQ KFVGEKLMRF SYPDIHFDMN LTYEKEAELM   240
QSHMMDQAIN NAITYLGAEA LHPLMQHPPS TIAEVAPVIS SAYSQVYHPN RIERPISRET   300
ADSHENNMDG PISLIRPKSR PQEREASPSN SCLDSTDSES SHDDHQSYQG HPALNPKRKQ   360
SPAYMKEDVK ALDTTKAPKG SLKDIYKVFN GEGEQIRAFK CEHCRVLFLD HVMYTIHMGC   420
HGYRDPLECN ICGYRSQDRY EFSSHIVRGE HTFH                              454

SEQ ID NO: 12              moltype = AA  length = 509
FEATURE                    Location/Qualifiers
source                     1..509
                           mol_type = protein
                           organism = Homo sapiens
SEQUENCE: 12
MEDIQTNAEL KSTQEQSVPA ESAAVLNDYS LTKSHEMENV DSGEGPANED EDIGDDSMKV    60
KDEYSERDEN VLKSEPMGNA EEPEIPYSYS REYNEYENIK LERHVVSFDS SRPTSGKMNC   120
DVCGLSCISF NVLMVHKRSH TGERPFQCNQ CGASFTQKGN LLRHIKLHTG EKPFKCHLCN   180
YACQRRDALT GHLRTHSVEK PYKCEFCGRS YKQRSSLEEH KERCRTFLQS TDPGDTASAE   240
ARHIKAEMGS ERALVLDRLA SNVAKRKSSM PQKFIGEKRH CFDVNYNSSY MYEKESELIQ   300
TRMMDQAINN AISYLGAEAL RPLVQTPPAP TSEMVPVISS MYPIALTRAE MSNGAPQELE   360
KKSIHLPEKS VPSERGLSPN NSGHDSTDTD SNHEERQNHI YQQNHMVLSR ARNGMPLLKE   420
VPRSYELLKP PPICPRDSVK VINKEGEVMD VYRCDHCRVL FLDYVMFTIH MGCHGFRDPF   480
ECNMCGYRSH DRYEFSSHIA RGEHRALLK                                    509

SEQ ID NO: 13              moltype = AA  length = 470
FEATURE                    Location/Qualifiers
source                     1..470
                           mol_type = protein
                           organism = Homo sapiens
SEQUENCE: 13
MEDIQTNAEL KSTQEQSVPA ESAAVLNDYS LTKSHEMENV DSGEGPANED EDIGDDSMKV    60
KDEYSERDEN VLKSEPMGNA EEPEIPYSYS REYNEYENIK LERHVVSFDS SRPTSGKMNC   120
DVCGLSCISF NVLMVHKRSH TGERPFQCNQ CGASFTQKGN LLRHIKLHTG EKPFKCHLCN   180
YACQRRDALT GHLRTHSASA EARHIKAEMG SERALVLDRL ASNVAKRKSS MPQKFIGEKR   240
HCFDVNYNSS YMYEKESELI QTRMMDQAIN NAISYLGAEA LRPLVQTPPA PTSEMVPVIS   300
SMYPIALTRA EMSNGAPQEL EKKSIHLPEK SVPSERGLSP NNSGHDSTDT DSNHEERQNH   360
IYQQNHMVLS RARNGMPLLK EVPRSYELLK PPPICPRDSV KVINKEGEVM DVYRCDHCRV   420
LFLDYVMFTI HMGCHGFRDP FECNMCGYRS HDRYEFSSHI ARGEHRALLK              470

SEQ ID NO: 14              moltype = AA  length = 470
FEATURE                    Location/Qualifiers
source                     1..470
                           mol_type = protein
                           organism = Homo sapiens
SEQUENCE: 14
MEDIQTNAEL KSTQEQSVPA ESAAVLNDYS LTKSHEMENV DSGEGPANED EDIGDDSMKV    60
KDEYSERDEN VLKSEPMGNA EEPEIPYSYS REYNEYENIK LERHVVSFDS SRPTSGKMNC   120
DVCGLSCISF NVLMVHKRSH TGERPFQCNQ CGASFTQKGN LLRHIKLHTG EKPFKCHLCN   180
YACQRRDALT GHLRTHSVEK PYKCEFCGRS YKQRSSLEEH KERCRTFLQS TDPGDTGEKR   240
HCFDVNYNSS YMYEKESELI QTRMMDQAIN NAISYLGAEA LRPLVQTPPA PTSEMVPVIS   300
SMYPIALTRA EMSNGAPQEL EKKSIHLPEK SVPSERGLSP NNSGHDSTDT DSNHEERQNH   360
IYQQNHMVLS RARNGMPLLK EVPRSYELLK PPPICPRDSV KVINKEGEVM DVYRCDHCRV   420
LFLDYVMFTI HMGCHGFRDP FECNMCGYRS HDRYEFSSHI ARGEHRALLK              470

SEQ ID NO: 15              moltype = AA  length = 431
FEATURE                    Location/Qualifiers
source                     1..431
                           mol_type = protein
                           organism = Homo sapiens
```

```
SEQUENCE: 15
MEDIQTNAEL KSTQEQSVPA ESAAVLNDYS LTKSHEMENV DSGEGPANED EDIGDDSMKV    60
KDEYSERDEN VLKSEPMGNA EEPEIPYSYS REYNEYENIK LERHVVSFDS SRPTSGKMNC   120
DVCGLSCISF NVLMVHKRSH TGERPFQCNQ CGASFTQKGN LLRHIKLHTG EKPFKCHLCN   180
YACQRRDALT GHLRTHSGEK RHCFDVNYNS SYMYEKESEL IQTRMMDQAI NNAISYLGAE   240
ALRPLVQTPP APTSEMVPVI SSMYPIALTR AEMSNGAPQE LEKKSIHLPE KSVPSERGLS   300
PNNSGHDSTD TDSNHEERQN HIYQQNHMVL SRARNGMPLL KEVPRSYELL KPPPICPRDS   360
VKVINKEGEV MDVYRCDHCR VLFLDYVMFT IHMGCHGFRD PFECNMCGYR SHDRYEFSSH   420
IARGEHRALL K                                                       431

SEQ ID NO: 16          moltype = AA  length = 475
FEATURE                Location/Qualifiers
source                 1..475
                       mol_type = protein
                       organism = Homo sapiens
SEQUENCE: 16
MEDIQTNAEL KSTQEQSVPA DDSMKVKDEY SERDENVLKS EPMGNAEEPE IPYSYSREYN    60
EYENIKLERH VVSFDSSRPT SGKMNCDVCG LSCISFNVLM VHKRSHTGER PFQCNQCGAS   120
FTQKGNLLRH IKLHTGEKPF KCHLCNYACQ RRDALTGHLR THSVEKPYKC EFCGRSYKQR   180
SSLEEHKERC RTFLQSTDPG DTASAEARHI KAEMGSERAL VLDRLASNVA KRKSSMPQKF   240
IGEKRHCFDV NYNSSYMYEK ESELIQTRMM DQAINNAISY LGAEALRPLV QTPPAPTSEM   300
VPVISSMYPI ALTRAEMSNG APQELEKKSI HLPEKSVPSE RGLSPNNSGH DSTDTDSNHE   360
ERQNHIYQQN HMVLSRARNG MPLLKEVPRS YELLKPPPIC PRDSVKVINK EGEVMDVYRC   420
DHCRVLFLDY VMFTIHMGCH GFRDPFECNM CGYRSHDRYE FSSHIARGEH RALLK        475

SEQ ID NO: 17          moltype = AA  length = 436
FEATURE                Location/Qualifiers
source                 1..436
                       mol_type = protein
                       organism = Homo sapiens
SEQUENCE: 17
MEDIQTNAEL KSTQEQSVPA DDSMKVKDEY SERDENVLKS EPMGNAEEPE IPYSYSREYN    60
EYENIKLERH VVSFDSSRPT SGKMNCDVCG LSCISFNVLM VHKRSHTGER PFQCNQCGAS   120
FTQKGNLLRH IKLHTGEKPF KCHLCNYACQ RRDALTGHLR THSAEARH IKAEMGSERA    180
LVLDRLASNV AKRKSSMPQK FIGEKRHCFD VNYNSSYMYE KESELIQTRM MDQAINNAIS   240
YLGAEALRPL VQTPPAPTSE MVPVISSMYP IALTRAEMSN GAPQELEKKS IHLPEKSVPS   300
ERGLSPNNSG HDSTDTDSNH EERQNHIYQQ NHMVLSRARN GMPLLKEVPR SYELLKPPPI   360
CPRDSVKVIN KEGEVMDVYR CDHCRVLFLD YVMFTIHMGC HGFRDPFECN MCGYRSHDRY   420
EFSSHIARGE HRALLK                                                  436

SEQ ID NO: 18          moltype = AA  length = 422
FEATURE                Location/Qualifiers
source                 1..422
                       mol_type = protein
                       organism = Homo sapiens
SEQUENCE: 18
MEDIQTNAEL KSTQEQSVPA ESAAVLNDYS LTKSHEMENV DSGEGPANED EDIGGERPFQ    60
CNQCGASFTQ KGNLLRHIKL HTGEKPFKCH LCNYACQRRD ALTGHLRTHS VEKPYKCEFC   120
GRSYKQRSSL EEHKERCRTF LQSTDPGDTA SAEARHIKAE MGSERALVLD RLASNVAKRK   180
SSMPQKFIGE KRHCFDVNYN SSYMYEKESE LIQTRMMDQA INNAISYLGA EALRPLVQTP   240
PAPTSEMVPV ISSMYPIALT RAEMSNGAPQ ELEKKSIHLP EKSVPSERGL SPNNSGHDST   300
DTDSNHEERQ NHIYQQNHMV LSRARNGMPL LKEVPRSYEL LKPPPICPRD SVKVINKEGE   360
VMDVYRCDHC RVLFLDYVMF TIHMGCHGFR DPFECNMCGY RSHDRYEFSS HIARGEHRAL   420
LK                                                                 422

SEQ ID NO: 19          moltype = AA  length = 263
FEATURE                Location/Qualifiers
source                 1..263
                       mol_type = protein
                       organism = Homo sapiens
SEQUENCE: 19
MEDIQTNAEL KSTQEQSVPA ESAAVLNDYS LTKSHEMENV DSGEGPANED EDIGDDSMKV    60
KDEYSERDEN VLKSEPMGNA EEPEIPYSYS REYNEYENIK LERHVVSFDS SRPTSGKMNC   120
DVCGLSCISF NVLMVHKRSH TGERPFQCNQ CGASFTQKGN LLRHIKLHTG EKPFKCHLCN   180
YACQRRDALT GHLRTHSVEK PYKCEFCGRS YKQRSSLEEH KERCRTFLQS TDPGDTGTGW   240
GWVELSHLGI RLQDLNVPWC RLH                                          263

SEQ ID NO: 20          moltype = AA  length = 582
FEATURE                Location/Qualifiers
source                 1..582
                       mol_type = protein
                       organism = Homo sapiens
SEQUENCE: 20
MHTPPALPRR FQGGGRVRTP GSHRQGKDNL ERDPSGGCVP DFLPQAQDSN HFIMESLFCE    60
SSGDSSLEKE FLGAPVGPSV STPNSQHSSP SRSLSANSIK VEMYSDEESS RLLGPDERLL   120
EKDDSVIVED SLSEPLGYCD GSGPEPHSPG GIRLPNGKLK CDVCGMVCIG PNVLMVHKRS   180
HTGERPFHCN QCGASFTQKG NLLRHIKLHS GEKPFKCPFC NYACRRRDAL TGHLRTHSVS   240
SPTVGKPYKC NYCGRSYKQQ STLEEHKERC HNYLQSLSTE AQALAGQPGD EIRDLEMVPD   300
SMLHSSSERP TFIDRLANSL TKRKRSTPQK FVGEKQMRFS LSDLPYDVNS GGYEKDVELV   360
```

```
AHHSLEPGFG SSLAFVGAEH LRPLRLPPTN CISELTPVIS SVYTQMQPLP GRLELPGSRE    420
AGEGPEDLAD GGPLLYRPRG PLTDPGASPS NGCQDSTDTE SNHEDRVAGW SLPQGPPPQP    480
PPTIWGRHSP AYAKEDPKPQ EGLLRGTPGP SKEVLRWGES GEPVKAFKCE HCRILFLDHV    540
MFTIHMGCHG FRDPFECNIC GYHSQDRYEF SSHIVRGEHK VG                       582

SEQ ID NO: 21           moltype = AA   length = 541
FEATURE                 Location/Qualifiers
source                  1..541
                        mol_type = protein
                        organism = Homo sapiens
SEQUENCE: 21
MDSRYLQLQL YLPSCSLLQG SGDSSLEKEF LGAPVGPSVS TPNSQHSSPS RSLSANSIKV     60
EMYSDEESSR LLGPDERLLE KDDSVIVEDS LSEPLGYCDG SGPEPHSPGG IRLPNGKLKC    120
DVCGMVCIGP NVLMVHKRSH TGERPFHCNQ CGASFTQKGN LLRHIKLHSG EKPFKCPFCN    180
YACRRRDALT GHLRTHSVSS PTVGKPYKCN YCGRSYKQQS TLEEHKERCH NYLQSLSTEA    240
QALAGQPGDE IRDLEMVPDS MLHSSSERPT FIDRLANSLT KRKRSTPQKF VGEKQMRFSL    300
SDLPYDVNSG GYEKDVELVA HHSLEPGFGS SLAFVGAEHL RPLRLPPTNC ISELTPVISS    360
VYTQMQPLPG RLELPGSREA GEGPEDLADG GPLLYRPRGP LTDPGASPSN GCQDSTDTES    420
NHEDRVAGWS LPQGPPPQPP PTIWGRHSPA YAKEDPKPQE GLLRGTPGPS KEVLRWGESG    480
EPVKAFKCEH CRILFLDHVM FTIHMGCHGF RDPFECNICG YHSQDRYEFS SHIVRGEHKV    540
G                                                                    541

SEQ ID NO: 22           moltype = AA   length = 23
FEATURE                 Location/Qualifiers
source                  1..23
                        mol_type = protein
                        organism = Homo sapiens
SEQUENCE: 22
FQCNQCGASF TQKGNLLRHI KLH                                             23

SEQ ID NO: 23           moltype = AA   length = 23
FEATURE                 Location/Qualifiers
source                  1..23
                        mol_type = protein
                        organism = Homo sapiens
SEQUENCE: 23
FHCNQCGASF TQKGNLLRHI KLH                                             23

SEQ ID NO: 24           moltype = AA   length = 23
FEATURE                 Location/Qualifiers
source                  1..23
                        mol_type = protein
                        organism = Homo sapiens
SEQUENCE: 24
FQCNQCGASF TQKGNLLRHI KLH                                             23

SEQ ID NO: 25           moltype = AA   length = 23
FEATURE                 Location/Qualifiers
source                  1..23
                        mol_type = protein
                        organism = Homo sapiens
SEQUENCE: 25
FHCNQCGASF TQKGNLLRHI KLH                                             23
```

SUBSTITUTED PHENYL OXAZOLONE COMPOUNDS

CROSS REFERENCE

This application is a continuation application filed under 35 U.S.C. 111 (a) which claims priority to International Patent Application No. PCT/US2024/028082, filed May 7, 2024, which claims priority to U.S. Provisional Application Ser. No. 63/500,727 filed May 8, 2023 and U.S. Provisional Application Ser. No. 63/632,070, filed Apr. 10, 2024, each incorporated herein in its entirety.

DESCRIPTION

The present invention generally relates to substituted phenyl oxazolone compounds that decrease the levels of the Ikaros, Helios. Aiolos, and Eos proteins. Provided herein are substituted phenyl oxazolone compounds, compositions comprising the compounds, and methods of use. The invention further pertains to pharmaceutical compositions comprising the compounds according to the invention that are useful for the treatment of proliferative disorders, such as cancer and viral infections.

REFERENCE TO SEQUENCE LISTING SUBMITTED ELECTRONICALLY VIA PATENT CENTER

Incorporated herein by reference in its entirety is a Sequence Listing entitled, "20241122 SEQ_14443USPCNT" comprising SEQ ID NO: 1 through SEQ ID NO: 25, which include nucleic acid and/or amino acid sequences disclosed herein. The Sequence Listing has been submitted herein in XML format via Patent Center, and thus constitutes both the paper and computer readable form thereof. The Sequence Listing was first created using WIPO Sequence on Nov. 22, 2024, and is 31,619 bytes.

BACKGROUND OF THE INVENTION

The Ikaros zinc finger family (IKZF) of transcription factors (TFs) play critical roles in lymphocyte development and function (Heizmann et al., 2018, Curr Opin Immunol. 51: 14-23). In mammals, the following five members of this family of TFs are expressed in immune cells: Ikaros (encoded by IKZF1), Helios (IKZF2), Aiolos (IKZF3), Eos (IKZF4), and Pegasus (IKZF5). The amino acid sequences of these proteins are highly homologous, with Ikaros and Aiolos, and Helios and Eos being the most homologous pairs, and Pegasus being the most distantly related IKZF member. These TFs serve both overlapping and unique functions in lymphocytes (Read et al., 2020, Immunological Reviews, 300:1). Reductions in the protein levels of IKZF TFs can boost antitumor T cell responses.

IKZF1 encodes Ikaros, which is broadly and abundantly expressed in human and mouse B, NK, and T lymphocyte populations, and moderately expressed in other immune cell types, including myeloid cells. In T cells, loss of Ikaros protein or expression of a dominant-negative protein relieves repression of loci related to the differentiation of the effector T cell state, resulting in increased expression of effector cytokines including IFN-γ, TNF-α, and GM-CSF (Lyon de Ana, et al., 2019, Journal of Immunology 202: 1112-1123; Heller et al., 2014, Journal of Immunology, 193: 3934-3946); Wang et al., 2020, Cell Transplantation, 29).

IKZF2 encodes Helios, which shows a more restricted expression profile limited to human and mouse regulatory T (Treg) cells, some CD8+ T cells and MAIT cells, and NK cells (Akimova et al., 2011, PLoS One, 6:e24226; Dias et al., 2017. Proceedings of the National Academy of Sciences USA, 114:E5434-E5443; Thornton and Shevach, 2019, Immunology, 158:161-170).

IKZF3 encodes Aiolos, which is broadly and abundantly expressed in human and mouse B lymphocytes, and broadly expressed at lower levels in T and NK cells. In T cells, Aiolos gene repression targets show a large amount of overlap with Ikaros target genes (Powell et al., 2019, Frontiers in Immunology, 10:1299). Compared to Ikaros, Aiolos may have a stronger effect on follicular helper T cell and T helper 17 type responses (Quintana et al., 2012, Nature Immunology, 13:770-777; Read et al., 2017 Journal of Immunology, 7:2377-2387), which have been implicated in tissue immune responses and, in some cases, antitumor immunity.

IKZF4 encodes Eos, which is abundantly expressed in Treg cells, and is also broadly expressed at low levels among B, NK, and T lymphocytes. In Treg cells, loss of Eos expression in FoxP3+ Treg cells drives improved antitumor responses in preclinical syngeneic tumor models (Gokhale et al., 2019, Journal of Autoimmunity, 105:102300). Additionally, Eos expression levels can increase after T cell activation in conventional CD4+ and CD8+ T cells, where it can limit effector T cell responses (Rieder et al., 2015, Journal of Immunology, 195:553-563).

Common functions shared among IKZF TFs relate to the suppression of gene expression in cells at specific loci. IKZF TFs can bind to genomic loci either as homodimers or heterodimers, such as Ikaros:Ikaros or Ikaros:Helios, respectively. These dimeric TFs both bind to DNA and interact with complexes that regulate histone acetylation and nucleosomes, which in turn results in gene expression modulation. Mechanistically. Ikaros, Helios, and Aiolos have each been shown to interact with the nucleosome-remodeling and deacetylase (NuRD) and Sin3 histone deacetylase (HDAC) complexes to repress gene expression (Zhang et al., 2011, Nature Immunology, 13:86-94; Georgopoulos et al., 2017, Genes and Development, 31: 439450). Similarly, Ikaros, Helios, and Aiolos all can associate with centromeric heterochromatin and contribute to the expression of genes located at centromeric loci (Brown et al., 1997, Cell, 91:845-854; Thompson et al., 2007, Immunity, 26:335-344). Eos co-operates with Ikaros, but not Aiolos, to interact with the transcriptional repressor C-terminal binding protein 1 (CtBPI) in lymphocytes (Koipally et al., 2002, Journal of Biological Chemistry, 277:27697-27705): Pan et al., 2009, Science, 325:1142-1146). Together, the overlapping functions of IKZF TFs may partially compensate for the loss or degradation of one or several TFs. Therefore, in cells that express multiple IKZF members, broad therapeutic degradation of this family of TFs would be expected to drive a stronger phenotypic change compared to selective degradation of one or two IKZF TFs.

In T cells and Treg cells, the shared roles of IKZF TFs in regulating a gene locus important for antitumor immune responses is exemplified by regulation of the gene encoding interleukin-2 (IL-2). Ikaros can directly bind to the IL-2 locus in CD4+ T cells and recruit HDAC complexes; loss of Ikaros results in increased IL-2 production by CD4+ and CD8+ T cells (Bandyopadhyay et al., 2007, Blood, 109: 2671-2672; Thomas et al., 2007, Journal of Immunology, 179: 7305-7315: O'Brien et al., 2014, Journal of Immunology, 192:5118-5129). Helios directly binds to the IL-2 locus in Treg cells to recruit HDAC complexes and enforce IL-2 gene silencing (Blaine et al., 2013, *Journal of Immunology*, 190:1008-1016). Eos also represses IL-2 expression in Treg cells and may act via a mechanism that involves interactions with the TF FoxP3 (Pan et al., 2009, Science, 325: 1142-1146; Sharma et al., 2013, *Immunity*, 38:998-1012). The role of direct Aiolos binding to the IL-2 loss is less clear, but siRNA knockdown of Aiolos in human Treg cells has been reported to increase IL-2 production (Gandhi et al., 2010, *Nature Immunology*, 11:846-853). In summary, the IKZF TFs act to modulate IL-2 production by multiple lymphocyte subtypes, particularly Treg cells in which all four of these IKZF TFs are abundantly expressed and IL-2 production is normally negligible.

Treg cells, which are marked by expression of the transcription factor FoxP3, are a subset of immunosuppressive lymphocytes that use several mechanisms to maintain immune homeostasis (Sakaguchi et al., 2020, *Annual Review of Immunology*, 38:541-566; Whibley et al., 2019, *Nature Immunology*, 20:386-396). Patients who have deleterious mutations in the gene encoding FoxP3 lack functional Treg cells and exhibit immune dysregulation, polyendocrinopathy, enteropathy, X-linked (IPEX) syndrome, a multi-organ autoimmune disorder. In the tumor microenvironment (TME), the activities of Treg cells are co-opted to promote and maintain an immunosuppressive state (Plitas and Rudensky, 2020, *Annual Review of Cancer Biology*, 4:459-477). By secreting suppressive molecules, sequestering cytokines (e.g., IL-2), and directly impeding T cell and antigen presenting cell activation. Treg cells can promote TME-mediated resistance to immunotherapy by modulating multiple axes in the cancer-immunity cycle (Chen and Mellman, 2013, Immunity, 39:1-10). In preclinical models, ablation of Treg cells results in the regression of aggressive, established tumors (Bos et al., 2013, *Journal of Experimental Medicine*, 210:2435-2466).

Once activated by a specific antigen, Treg cells can suppress responder T cells in an antigen-nonspecific and bystander manner in vitro (Takahashi et al., 1998, *Int Immunol*, 10:1969-80; Thornton et al., 1998, *J Exp Med* 188:287-96). FoxP3+CD25+CD4+ Treg cells are capable of suppressing a wide range of antitumor immune responses involving CD4+ helper T cells, CD8+ T cells, natural killer cells, and natural killer T cells (Tanaka et al., 2017, *Cell Research* 27:109-118). In preclinical models, the intratumoral depletion of CD25+CD4+ Treg cells induced regression of established tumors with a change in the cytokine milieu at tumor sites (Yu et al., 2005, *J Exp Med* 201: 779-91). In addition, transfer of Treg cell-depleted CD4+ T cells markedly augmented antitumor immune responses compared with the transfer of Treg cell-sufficient CD4+ T cells (Antony et al., 2005, *J Immunol* 174:2591-601). Tumor-infiltrating Treg cells activated by either tumor-derived self-antigens or tumor-associated antigens can similarly suppress specific antitumor immune responses.

Clinically, increased Treg cell frequencies in the TME are correlated with worse outcomes in multiple solid tumor indications (Shang et al., 2015, Scientific Reports, 5:15179). Moreover, correlations between PD-L1+ Treg cell frequencies and responses to anti-PD-1 therapy in non-small cell lung cancer (NSCLC) patients (Wu et al., 2018, Journal of Thoracic Oncology, 13:521-532) highlight the therapeutic potential of Treg cell targeting in the TME. Modulation of the activities of key factors to control Treg cell differentiation could represent a potential therapeutic strategy for the treatment of certain diseases, including cancer and viral infections.

Furthermore, removal of FoxP3+ Treg cells was also reported to enhance vaccine-induced antitumor T-cell responses (Nishikawa et al., 2010, *Int J. Cancer* 127: 759-767), suggesting that decreasing Helios levels could be beneficial in boosting the efficacy of cancer vaccines. Besides anti-tumor immunotherapy, during viral infections, Treg cells can limit the immunopathology resulting from excessive inflammation, yet potentially inhibit effective antiviral T cell responses and promote virus persistence (Schmitz et al., 2013, *PLOS Pathogens* 9: e1003362). Chronic, but not acute, infection of mice with lymphocytic choriomeningitis virus results in a marked expansion of FoxP3+ Treg cells, implying a potential mechanism that certain infectious agents could evade host immune responses by activation and expansion of Treg cells (Punkosdy et al., 2011, *PNAS* 108: 3677-3682). Treatment benefits could be achieved by decreasing Helios levels in activated Treg cells in a context relevant to chronic viral infections.

Approaches to targeting tumor Treg cells include antibody-mediated depletion and/or functional modulation (Tanaka and Sakaguchi, 2019, *European Journal of Immunology*, 49:1140-1146), as well as small molecule-mediated "reprogramming" of the Treg cell immunosuppressive phenotype by altering gene expression in these cells (Kim et al., 2015, Science, 350:334-339: Sebastian et al., 2016, *Journal of Immunology*, 196:144-155). Mice with Treg cells engineered to lack Helios do not develop IPEX-like immunopathology characteristic of FoxP3-deficiency or complete Treg cell ablation, but instead have Treg cells that display a more T effector-like transcriptional program (Fu et al., 2012, *Nature Immunology*, 13: 972-980: Yates et al., 2018, *Proceedings of the National Academy of Sciences USA*, 115: 2162-2167). Importantly, Helios controls activities of Treg cells that are critical in the TME as mice with Helios-deficient Treg cells show improved control of B16F10 and MC38 tumors (Nakagawa et al., 2016, *Proceedings of the National Academy of Sciences USA*, 113:6248-6253). Therefore, therapeutic modulation of Helios has the potential to reprogram tumor Treg cells towards a more effector-like phenotype to drive antitumor immunity. Notably, Eos also drives immunosuppressive Treg cell activity in the TME in preclinical tumor models, as mice lacking Eos expression in FoxP3 Treg cells more effectively control syngeneic tumors compared to controls (Gokhale et al., 2019, *Journal of Autoimmunity*, 105:102300). Humans with germline loss-of-function IKZF2 mutations similarly do not exhibit IPEX-like symptoms (including diabetes, dermatitis, hepatic inflammation, and systemic lymphadenopathy), but instead manifest immunophenotypes related to enhanced T cell activation and proinflammatory cytokine production (Hetemtiki et al., 2021, Science Immunology, 6:eabe3454; Shahin et al., 2021, Science Immunology, 6:eabe3981). These data indicate that reduction of Helios and Eos protein levels in Treg cells would make them less suppressive of antitumor T cell responses in patients with solid tumors.

Small molecules that degrade Ikaros and Aiolos in Treg cells can also reduce the suppressive functions of these cells in vitro (Galustian et al., 2008, *Cancer Immunology Immunotherapy*, 58:1033-1045). In engineered mouse models, the Ikaros and Aiolos degrader lenalidomide can modestly increase antitumor immune responses against highly immunogenic syngeneic tumors (Geng et al., 2022, *Cell Chemical Biology*, 29:1260-1272). Ikaros- and Aiolos-targeted degraders have also been tested clinically in patients with solid tumors, sometimes resulting in modest responses of stable disease. These studies included avadomide (CC-122) in advanced malignancies (Rasco et al., 2019, *Clin Cancer*

*Research*, 25:90-98), lenalidomide (Semeraro et al., 2013, *OncoImmunology*, 2:11), and pomalidomide (Cooney et al., 2012, *Cancer Chemotherapy and Pharmacology*, 70, 755). Additionally, lenalidomide has been shown to augment T and NK cell functions in preclinical and clinical studies (Hideshima et al., Leukemia, 2021; D'Souza et al., Frontiers in Immunology, 2021).

In summary, the four IKZF TFs, Ikaros, Helios, Aiolos, and Eos, are abundantly expressed in Treg cells. Combined reduction of the individual protein levels of these four TFs in Treg cells would better reverse the immunosuppressive program, including repression of IL-2 transcription, compared to approaches that selectively target single IKZF TFs or pairs of TFs, i.e., Ikaros and Aiolos or Helios and Eos. Beyond Treg cells, a pan-IKZF1-4 degrader would be expected to increase conventional CD4+ and CD8+ T cell effector functions and boost NK cell activity to drive robust antitumor responses in patients.

There remains a need for therapies that can decrease the levels of the four IKZF1-4 proteins Ikaros, Helios, Aiolos, and Eos.

The present invention fills the foregoing need by providing a compound that is useful to decrease the levels of the four IKZF1-4 proteins Ikaros, Helios, Aiolos, and Eos.

SUMMARY OF THE INVENTION

The present invention provides substituted phenyl oxazolone compounds of Formula (I), including stereoisomers, tautomers, salts, and prodrugs thereof, which are useful to decrease the levels of the four proteins Ikaros, Helios, Aiolos, and Eos protein levels.

The present invention also provides pharmaceutical compositions comprising a compound of Formula (I), stereoisomers, tautomers, pharmaceutically acceptable salts, or prodrugs thereof; and a pharmaceutically acceptable carrier.

The present invention also provides a method of treating a disease or disorder by decreasing the levels of the four IKZF1-4 proteins Ikaros, Helios, Aiolos, and Eos, the method comprising administering to a patient a compound of Formula (I), stereoisomers, tautomers, pharmaceutically acceptable salts, or prodrugs thereof.

The present invention also provides processes and intermediates for making the compounds of Formula (I), stereoisomers, tautomers, or salts thereof.

The present invention also provides the use of a compound of Formula (I), or stereoisomers, tautomers, pharmaceutically acceptable salts, or prodrugs thereof, for the manufacture of a medicament to decrease Ikaros, Helios, Aiolos, and Eos protein levels, for the treatment of certain diseases, including cancer and viral infections.

The compounds of Formula (I) and compositions comprising a compound of Formula (I) may be used in treating, preventing, or curing various proliferative disorders, such as cancer. Pharmaceutical compositions comprising the compounds are useful in treating, preventing, or slowing the progression of diseases or disorders in a variety of therapeutic areas, such as cancer.

The compounds of Formula (I) and compositions comprising a compound of Formula (I) may be used in treating, preventing, or curing viral infections. Pharmaceutical compositions comprising a compound are useful in treating, preventing, or slowing the progression of diseases or disorders, such as viral infections.

These and other features of the invention will be set forth in expanded form as the disclosure continues.

DETAILED DESCRIPTION

Applicants have found substituted phenyl oxazolone compounds that decreases the levels of the Ikaros, Helios, Aiolos, and Eos proteins. The substituted phenyl oxazolone compounds are believed to facilitate the interactions of Ikaros, Helios, Aiolos, and Eos proteins with the corresponding E3 ubiquitin ligase complex (Cullin4-Cereblon, CUL4-CRBN), with concomitant degradation of the Ikaros, Helios, Aiolos, and Eos proteins. The compounds decrease the levels of Ikaros protein, Helios protein, Aiolos protein, and Eos protein. The compounds are useful for the treatment of certain diseases, including cancer and viral infections. The compounds are provided to be useful as pharmaceuticals with desirable stability, bioavailability, therapeutic index, and toxicity values that are important to their drugability.

The first aspect of the present invention provides compounds of Formula (I):

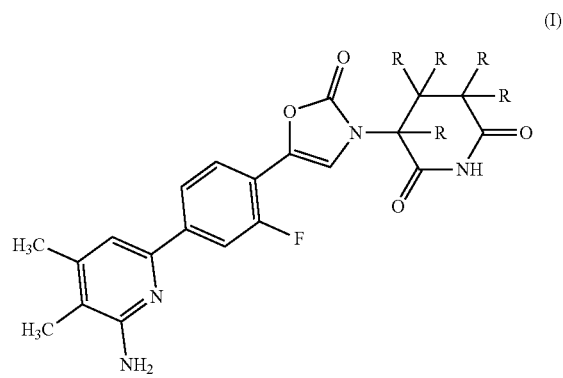

or stereoisomers, tautomers, or salts thereof, wherein each R is independently is hydrogen (H) or deuterium (D).

One embodiment provides compounds of Formula (I), or stereoisomers, tautomers, or pharmaceutically acceptable salts thereof.

One embodiment provides compounds of Formula (I), or stereoisomers or tautomers thereof.

One embodiment provides salts of the compounds of Formula (I), or stereoisomers or tautomers thereof.

One embodiment provides pharmaceutically acceptable salts of the compounds of Formula (I), or stereoisomers or tautomers thereof.

The second aspect of the present invention provides a compound of Formula (I) having the structure of the compound of Formula (Ia):

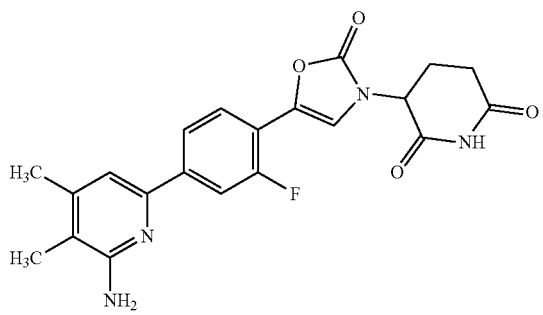

or stereoisomers, tautomers, or salts thereof.

One embodiment provides a compound of Formula (Ia), or stereoisomers, tautomers, or pharmaceutically acceptable salts thereof.

One embodiment provides a compound of Formula (Ia), or stereoisomers or tautomers thereof.

One embodiment provides a salt of the compound of Formula (Ia), or stereoisomers or tautomers thereof.

One embodiment provides a pharmaceutically acceptable salt of the compound of Formula (Ia), or stereoisomers or tautomers thereof.

The third aspect of the present invention provides a compound of Formula (I) having the structure of the compound of Formula (Ib):

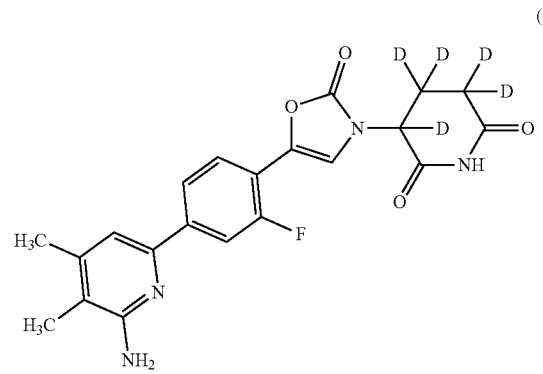

or stereoisomers, tautomers, or salts thereof.

One embodiment provides a compound of Formula (Ib), or stereoisomers, tautomers, or pharmaceutically acceptable salts thereof.

One embodiment provides a compound of Formula (Ib), or stereoisomers or tautomers thereof.

One embodiment provides a salt of the compound of Formula (Ib), or stereoisomers or tautomers thereof.

One embodiment provides a pharmaceutically acceptable salt of the compound of Formula (Ib), or stereoisomers or tautomers thereof.

One embodiment provides a compound of Formula (I), or stereoisomers, tautomers, or pharmaceutically acceptable salts thereof wherein at least one R is D.

One embodiment provides a compound of Formula (I), or stereoisomers, tautomers, or pharmaceutically acceptable salts thereof wherein at least two R are D.

One embodiment provides a compound of Formula (I), or stereoisomers, tautomers, or pharmaceutically acceptable salts thereof wherein at least three R are D.

One embodiment provides a compound of Formula (I), or stereoisomers, tautomers, or pharmaceutically acceptable salts thereof wherein at least four R are D.

One embodiment provides a compound of Formula (I), or stereoisomers, tautomers, or salts thereof, wherein said compound is selected from 3-(5-(4-(6-amino-4,5-dimethylpyridin-2-yl)-2-fluorophenyl)-2-oxooxazol-3(2H)-yl)piperidine-2,6-dione and 3-(5-(4-(6-amino-4,5-dimethylpyridin-2-yl)-2-fluorophenyl)-2-oxooxazol-3(2H)-yl)piperidine-2,6-dione-3,4,4,5,5-$d_5$.

One embodiment provides a compound of Formula (Ia), or tautomers or salts thereof, wherein said compound is (S)-3-(5-(4-(6-amino-4,5-dimethylpyridin-2-yl)-2-fluorophenyl)-2-oxooxazol-3(2H)-yl)piperidine-2,6-dione. Additionally, included in this embodiment are one or more pharmaceutically acceptable salts.

One embodiment provides a compound of Formula (Ia), or tautomers or salts thereof, wherein said compound is (R)-3-(5-(4-(6-amino-4,5-dimethylpyridin-2-yl)-2-fluorophenyl)-2-oxooxazol-3(2H)-yl)piperidine-2,6-dione. Additionally, included in this embodiment are one or more pharmaceutically acceptable salts.

One embodiment provides a compound of Formula (Ib), or tautomers or salts thereof, wherein said compound is (S)-3-(5-(4-(6-amino-4,5-dimethylpyridin-2-yl)-2-fluorophenyl)-2-oxooxazol-3(2H)-yl)piperidine-2,6-dione-3,4,4,5,5-$d_5$. Additionally, included in this embodiment are one or more pharmaceutically acceptable salts.

One embodiment provides a compound of Formula (Ib), or tautomers or salts thereof, wherein said compound is (R)-3-(5-(4-(6-amino-4,5-dimethylpyridin-2-yl)-2-fluorophenyl)-2-oxooxazol-3(2H)-yl)piperidine-2,6-dione-3,4,4,5,5-$d_5$. Additionally, included in this embodiment are one or more pharmaceutically acceptable salts.

One embodiment provides a compound of Formula (I) having the structure:

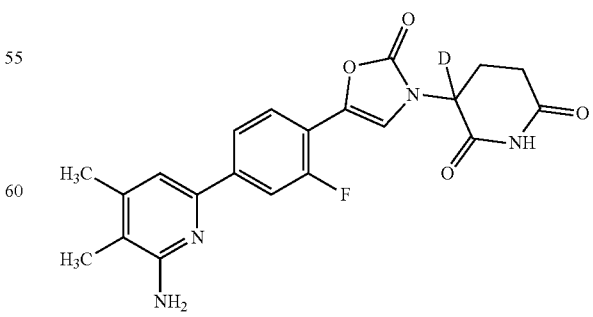

or stereoisomers, tautomers, or salts thereof.

One embodiment provides a compound of Formula (I) having the structure:

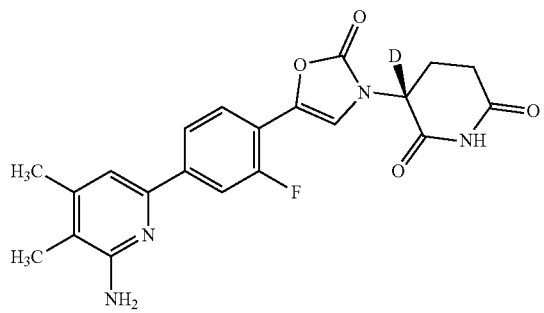 [SMILES: [2H][C@@]1(n2cc(-c3ccc(-c4cc(C)c(C)c(N)n4)cc3F)oc2=O)CCC(=O)NC1=O]

or tautomers or salts thereof.

The compounds of Formula (I) or stereoisomers, tautomers, or salts thereof, are useful to decrease the levels of the four IKZF1-4 proteins Ikaros, Helios, Aiolos, and Eos.

As used herein, "to decrease the level" of one of the IKZF1-4 proteins refers to reducing the level of the protein by the degradation and/or inactivation and/or inhibition and/or reducing the expression levels of the protein, or a combination thereof, compared to the initial protein level prior to contact or treatment with a compound of Formula (I) or stereoisomers, tautomers, or salts thereof.

Various methods can be employed to measure the decreases in the protein levels of the IKZF1-4 proteins, including the following assays described hereinbelow: (i) IKZF1: Human CD8⁺ T Cell Reprogramming Assay; (ii) IKZF2: Jurkat Cellular Degradation Assay: (iii) IKZF3: Human CD8⁺ T Cell Reprogramming Assay; and (iv) IKZF4: Human T Regulatory Cell Reprogramming Assay.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compound and/or salts thereof" refers to the compound, at least one salt of the compound, or a combination thereof. For example, a compound of Formula (I) and/or salts thereof includes a compound of Formula (I); a salt of a compound of Formula (I); a compound of Formula (I) and one or more salts of a compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,  is used in structural formulas herein to depict the bond that is the point of attachment of the moiety or substituent to the core or backbone structure.

The term "amino" refers to the group —NH.

The term "oxo" refers to the group =O.

The compounds of the present invention include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, the term "tautomer" refers to each of two or more isomers of a compound that exist together in equilibrium and are readily interchanged by migration of an atom or group within the molecule. For example, one skilled in the art would readily understand that a 1,2,3-triazole exists in two tautomeric forms as defined above:

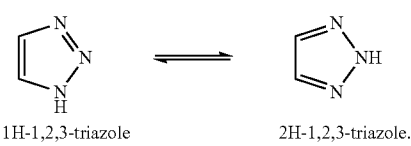

1H-1,2,3-triazole      2H-1,2,3-triazole.

Thus, this disclosure is intended to cover all possible tautomers even when a structure depicts only one of them. For example, a compound of Formula (I) can exist in tautomer forms:

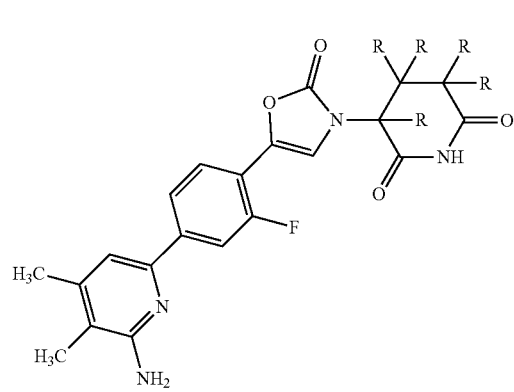
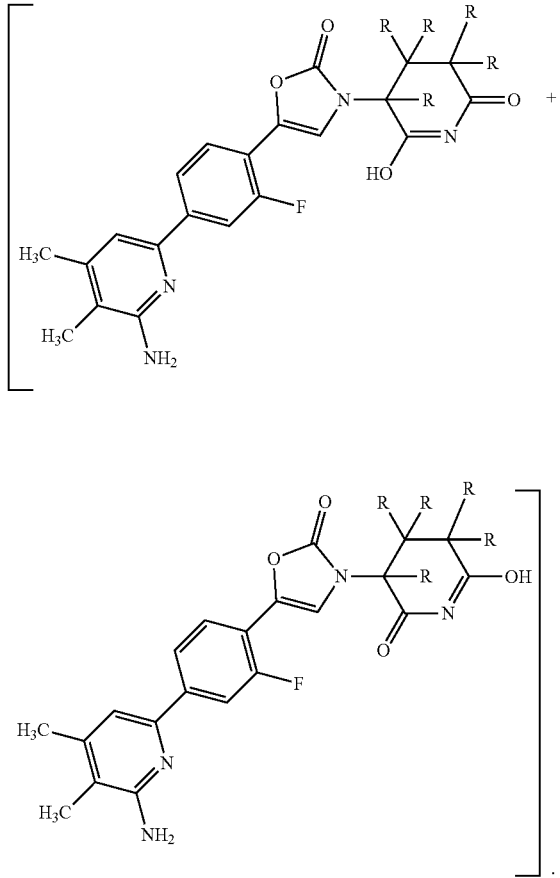
Likewise, the compound of Formula (Ia) can exist in tautomer forms:
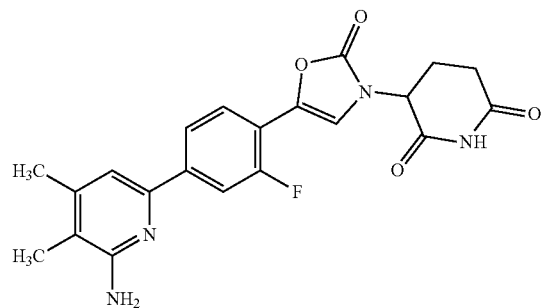
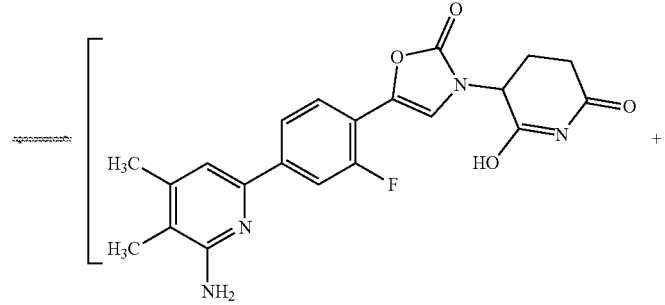
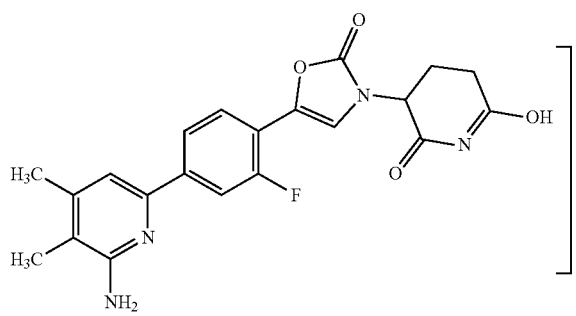

Other examples of tautomer forms include:

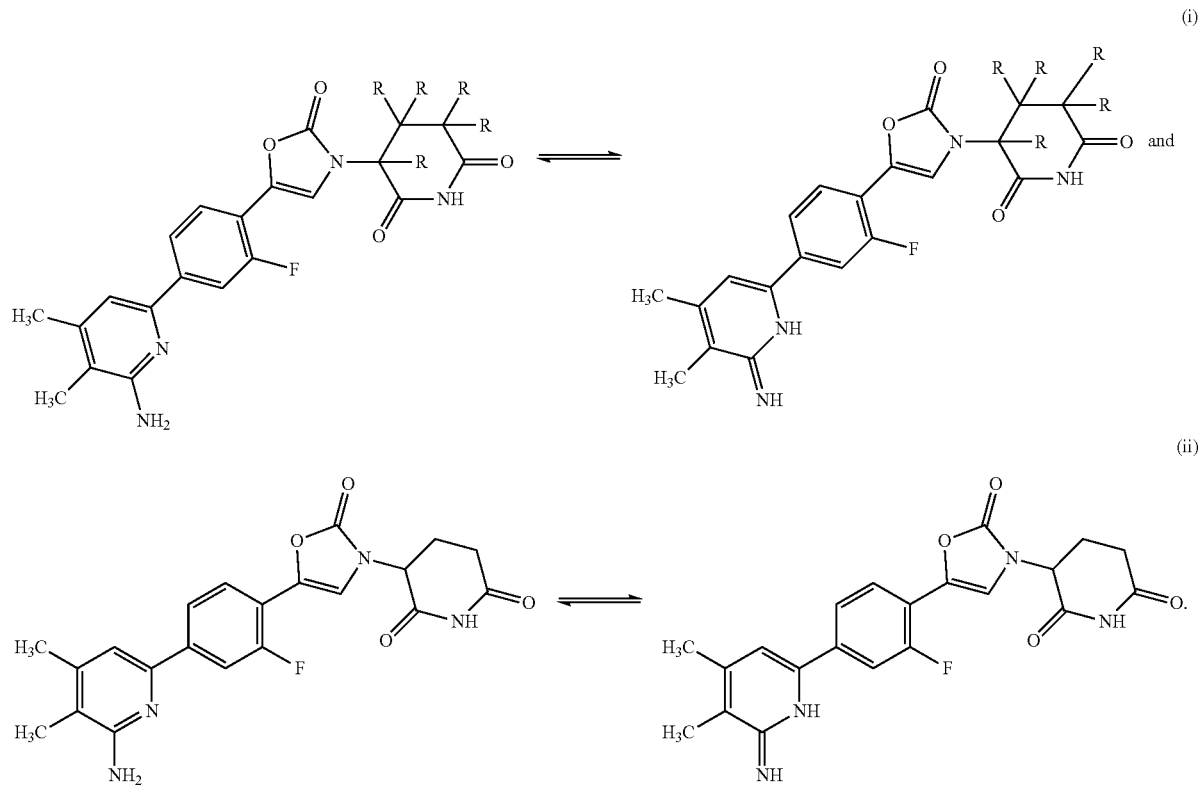

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic salt(s) formed with inorganic and/or organic acids. Pharmaceutically acceptable (i.e., non-toxic, physiologically acceptable) salts are preferred. However, other salts may be useful. e.g., in isolation or purification steps which may be employed during preparation, and thus, are contemplated within the scope of the invention. Salts of the compound of the Formula (I) may be formed, for example, by reacting the compound of the Formula (I) with an amount of acid, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula (I) can be provided as amorphous solids or crystalline solids. Lyophilization can be employed to provide the compounds of Formula (I) as solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review Drug Discovery*, 17, 559-587 (2018).

In addition, a compound of Formula (I), subsequent to its preparation, can be isolated and purified to obtain a composition containing an amount by weight equal to or greater than 99% of a compound of Formula (I) ("substantially pure"), which is then used or formulated as described herein. Such "substantially pure" compound of Formula (I) is also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody a stable compound.

The terms "IKZF1 degrader" and "Ikaros degrader" refer to an agent capable of reducing the level of the IKZF1 protein by degradation and/or inactivation and/or inhibition and/or reducing the expression levels of the IKZF1 protein, or a combination thereof.

The terms "IKZF2 degrader" and "Helios degrader" refer to an agent capable of reducing the level of the IKZF2 protein by degradation and/or inactivation and/or inhibition and/or reducing the expression levels of the IKZF2 protein, or a combination thereof.

The terms "IKZF3 degrader" and "Aiolos degrader" refer to an agent capable of reducing the level of the IKZF3 protein by degradation and/or inactivation and/or inhibition and/or reducing the expression levels of the IKZF3 protein, or a combination thereof.

The terms "IKZF4 degrader" and "Eos degrader" refer to an agent capable of reducing the level of the IKZF4 protein by degradation and/or inactivation and/or inhibition and/or reducing the expression levels of the IKZF4 protein, or a combination thereof.

The term "IKZF1-4 proteins" refers to the Ikaros (IKZF1), Helios (IKZF2), Aiolos (IKZF3), and Eos (IKZF4) proteins.

The term "pan IKZF1-4 degrader" refers to an agent capable of decreasing the protein levels of the four IKZF1-4 proteins Ikaros, Helios, Aiolos, and Eos.

As used herein, "Ikaros" protein is encoded by the IKZF1 gene. Ikaros is also known as IKAROS family zinc finger 1, ZNFN1A1, zinc finger protein, subfamily 1A, 1, Ikaros family zinc finger protein 1, IK1, lymphoid transcription factor LyF-1, Hs, 54452, PPP1R92, protein phosphatase 1, regulatory subunit 92, PRO0758, CVID13, and CLL associated antigen KW-6. "Ikaros" protein includes isoforms encoded by the following human isoforms listed below.

```
Isoform 1 (UniPort Q13422-1)
                                        (SEQ ID NO: 1)
MDADEGQDMSQVSGKESPPVSDTPDEGDEPMPIPEDLSTTSGGQQ

SSKSDRVVASNVKVETQSDEENGRACEMNGEECAEDLRMLDASGE

KMNGSHRDQGSSALSGVGGIRLPNGKLKCDICGIICIGPNVLMVH

KRSHTGERPFQCNQCGASFTQKGNLLRHIKLHSGEKPFKCHLCNY

ACRRRDALTGHLRTHSVGKPHKCGYCGRSYKQRSSLEEHKERCHN

YLESMGLPGTLYPVIKEETNHSEMAEDLCKIGSERSLVLDRLASN

VAKRKSSMPQKFLGDKGLSDTPYDSSASYEKENEMMKSHVMDQAI

NNAINYLGAESLRPLVQTPPGGSEVVPVISPMYQLHKPLAEGTPR

SNHSAQDSAVENLLLLSKAKLVPSEREASPSNSCQDSTDTESNNE

EQRSGLIYLTNHIAPHARNGLSLKEEHRAYDLLRAASENSQDALR
```

```
VVSTSGEQMKVYKCEHCRVLFLDHVMYTIHMGCHGFRDPFECNMC

GYHSQDRYEFSSHITRGEHRFHMS

Isoform 2 (UniProt Q13422-2)
                                        (SEQ ID NO: 2)
MDADEGQDMSQVSGKESPPVSDTPDEGDEPMPIPEDLSTTSGGQQ

SSKSDRVVGERPFQCNQCGASFTQKGNLLRHIKLHSGEKPFKCHL

CNYACRRRDALTGHLRTHSVGKPHKCGYCGRSYKQRSSLEEHKER

CHNYLESMGLPGTLYPVIKEETNHSEMAEDLCKIGSERSLVLDRL

ASNVAKRKSSMPQKFLGDKGLSDTPYDSSASYEKENEMMKSHVMD

QAINNAINYLGAESLRPLVQTPPGGSEVVPVISPMYQLHKPLAEG

TPRSNHSAQDSAVENLLLLSKAKLVPSEREASPSNSCQDSTDTES

NNEEQRSGLIYLTNHIAPHARNGLSLKEEHRAYDLLRAASENSQD

ALRVVSTSGEQMKVYKCEHCRVLFLDHVMYTIHMGCHGFRDPFEC

NMCGYHSQDRYEFSSHITRGEHRFHMS

Isoform 3 (UniProt Q13422-3)
                                        (SEQ ID NO: 3)
MDADEGQDMSQVSGKESPPVSDTPDEGDEPMPIPEDLSTTSGGQQ

SSKSDRVVASNVKVETQSDEENGRACEMNGEECAEDLRMLDASGE

KMNGSHRDQGSSALSGVGGIRLPNGKLKCDICGIICIGPNVLMVH

KRSHTGERPFQCNQCGASFTQKGNLLRHIKLHSGEKPFKCHLCNY

ACRRRDALTGHLRTHSGDKGLSDTPYDSSASYEKENEMMKSHVMD

QAINNAINYLGAESLRPLVQTPPGGSEVVPVISPMYQLHKPLAEG

TPRSNHSAQDSAVENLLLLSKAKLVPSEREASPSNSCQDSTDTES

NNEEQRSGLIYLTNHIAPHARNGLSLKEEHRAYDLLRAASENSQD

ALRVVSTSGEQMKVYKCEHCRVLFLDHVMYTIHMGCHGFRDPFEC

NMCGYHSQDRYEFSSHITRGEHRFHMS

Isoform 4 (UniProt Q13422-4)
                                        (SEQ ID NO: 4)
MDADEGQDMASNVKVETQSDEENGRACEMNGEECAEDLRMLDASG

EKMNGSHRDQGSSALSGVGGIRLPNGKLKCDICGIICIGPNVLMV

HKRSHTGERPFQCNQCGASFTQKGNLLRHIKLHSGEKPFKCHLCN

YACRRRDALTGHLRTHSGDKGLSDTPYDSSASYEKENEMMKSHVM

DQAINNAINYLGAESLRPLVQTPPGGSEVVPVISPMYQLHKPLAE

GTPRSNHSAQDSAVENLLLLSKAKLVPSEREASPSNSCQDSTDTE

SNNEEQRSGLIYLTNHIAPHARNGLSLKEEHRAYDLLRAASENSQ

DALRVVSTSGEQMKVYKCEHCRVLFLDHVMYTIHMGCHGFRDPFE

CNMCGYHSQDRYEFSSHITRGEHRFHMS

Isoform 7 (UniProt Q13422-7)
                                        (SEQ ID NO: 5)
MDADEGQDMSQVSGKESPPVSDTPDEGDEPMPIPEDLSTTSGGQQ

SSKSDRVVASNVKVETQSDEENGRACEMNGEECAEDLRMLDASGE

KMNGSHRDQGSSALSGVGGIRLPNGKLKCDICGIICIGPNVLMVH

KRSHTGERPFQCNQCGASFTQKGNLLRHIKLHSGEKPFKCHLCNY

ACRRRDALTGHLRTHSVIKEETNHSEMAEDLCKIGSERSLVLDRL

ASNVAKRKSSMPQKFLGDKGLSDTPYDSSASYEKENEMMKSHVMD
```

```
QAINNAINYLGAESLRPLVQTPPGGSEVVPVISPMYQLHKPLAEG

TPRSNHSAQDSAVENLLLLSKAKLVPSEREASPSNSCQDSTDTES

NNEEQRSGLIYLTNHIAPHARNGLSLKEEHRAYDLLRAASENSQD

ALRVVSTSGEQMKVYKCEHCRVLFLDHVMYTIHMGCHGFRDPFEC

NMCGYHSQDRYEFSSHITRGEHRFHMS

Isoform 8 (UniProt Q13422-8)
                                        (SEQ ID NO: 6)
MDADEGQDMSQVSGKESPPVSDTPDEGDEPMPIPEDLSTTSGGQQ

SSKSDRVVASNVKVETQSDEENGRACEMNGEECAEDLRMLDASGE

KMNGSHRDQGSSALSGVGGIRLPNGKLKCDICGIICIGPNVLMVH

KRSHTGERPFQCNQCGASFTQKGNLLRHIKLHSGEKPFKCHLCNY

ACRRRDALTGHLRTHSVIKEETNHSEMAEDLCKIGSEISRAGQTS

K
```

The "Ikaros" protein isoforms 1, 2, 3, 4, 7, and 8 listed above includes the degron FQCNQC-GASFTQKGNLLRHIKLH (SEQ ID NO: 22), which is the same as the degron for the "Aiolos" protein. Ikaros protein also includes isoforms encoded by amino acid sequences Q13422-5 and Q13422-6.

As used herein, "Helios" protein refers a protein that is a member of the Ikaros family of zinc finger proteins. In humans, Helios is encoded by the IKZF2 gene. Helios is also known as IKAROS family zinc finger 2, ANF1A2, ZNF1A2, ZNFN1A2, zinc finger protein, subfamily 1 A, 2, and Ikaros family zinc finger protein 2. As used herein Helios protein includes various isoform, which includes the isoforms listed below.

```
Isoform 1 (UniProt Q9UKS7-1)
                                        (SEQ ID NO: 7)
METEAIDGYITCDNELSPEREHSNMAIDLTSSTPNGQHASPSHMT

STNSVKLEMQSDEECDRKPLSREDEIRGHDEGSSLEEPLIESSEV

ADNRKVQELQGEGGIRLPNGKLKCDVCGMVCIGPNVLMVHKRSHT

GERPFHCNQCGASFTQKGNLLRHIKLHSGEKPFKCPFCSYACRRR

DALTGHLRTHSVGKPHKCNYCGRSYKQRSSLEEHKERCHNYLQNV

SMEAAGQVMSHHVPPMEDCKEQEPIMDNNISLVPFERPAVIEKLT

GNMGKRKSSTPQKFVGEKLMRFSYPDIHFDMNLTYEKEAELMQSH

MMDQAINNAITYLGAEALHPLMQHPPSTIAEVAPVISSAYSQVYH

PNRIERPISRETADSHENNMDGPISLIRPKSRPQEREASPSNSCL

DSTDSESSHDDHQSYQGHPALNPKRKQSPAYMKEDVKALDTTKAP

KGSLKDIYKVFNGEGEQIRAFKCEHCRVLFLDHVMYTIHMGCHGY

RDPLECNICGYRSQDRYEFSSHIVRGEHTFH

Isoform 2 (UniProt Q9UKS7-2)
                                        (SEQ ID NO: 8)
METEAIDGYITCDNELSPEREHSNMAIDLTSSTPNGQHASPSHMT

STNSVKLEMQSDEECDRKPLSREDEIRGHDEGSSLEEPLIESSEV

ADNRKVQELQGEGGIRLPNGERP**FHCNQCGASFTQKGNLLRHIKL

H**SGEKPFKCPFCSYACRRRDALTGHLRTHSVGKPHKCNYCGRSYK

QRSSLEEHKERCHNYLQNVSMEAAGQVMSHHVPPMEDCKEQEPIM

DNNISLVPFERPA VIEKLTGNMGKRKSSTPQKFVGEKLMRFSYP

DIHFDMNLTYEKEAELMQSHMMDQAINNAITYLGAEALHPLMQHP

PSTIAEVAPVISSAYSQVYHPNRIERPISRETADSHENNMDGPIS

LIRPKSRPQEREASPSNSCLDSTDSESSHDDHQSYQGHPALNPKR

KQSPAYMKEDVKALDTTKAPKGSLKDIYKVENGEGEQIRAFKCEH

CRVLFLDHT/MYTIHMGCHGYRDPLECNICGYRSQDRYE FSSHI

VRG EHTFH

Isoform 4 (UniProt Q9UKS7-4)
                                        (SEQ ID NO: 9)
METEAIDGYITCDNELSPEREHSNMAIDLTSSTPNGQHASPSHMT

STNSVKLEMQSDEECDRKPLSREDEIRGHDEGSSLEEPLIESSEV

ADNRKVQELQGEGGIRLPNGERP**FHCNQCGASFTQKGNLLRHIKL

H**SGEKPFKCPFCSYACRRRDALTGHLRTHSVGKPHKCNYCGRSYK

QRSSLEEHKERCHNYLQNVSMEAAGQVMSHHGEKLMRFSYPDIHF

DMNLTYEKEAELMQSHMMDQAINNAITYLGAEALHPLMQHPPSTI

AEVAPVISSAYSQVYHPNRIERPISRETADSHENNMDGPISLIRP

KSRPQEREASPSNSCLDSTDSESSHDDHQSYQGHPALNPKRKQSP

AYMKEDVKALDTTKAPKGSLKDIYKVFNGEGEQRAFKCEHCRVLF

LDHVMYTIHMGCHGYRDPLECNICGYRSQDRYEF SSHIVRGEHT

FH

Isoform 6 (UniProt Q9UKS7-6)
                                        (SEQ ID NO: 10)
METEAIDGYITCDNELSPEREHSNMAIDLTSSTPNGQHASPSHMT

STNSVKLEMQSDEECDRKPLSREDEIRGHDEGSSLEEPLIESSEV

ADNRKVQELQGEGGIRLPNGKLKCDVCGMVCIGPNVLMVHKRSHT

GERPFHCNQCGASFTQKGNLLRHIKLHSGEKPFKCPFCSYACRRR

DALTGHLRTHSVGKPHKCNYCGRSYKQRSSLEEHKERCHNYLQNV

SMEAAGQVMSHHDS

Isoform 7 (UniProt Q9UKS7-7)
                                        (SEQ ID NO: 11)
METEAIDGYITCDNELSPEREHSNMAIDLTSSTPNGQHASPSHMT

STNSVKLEMQSDEECDRKPLSREDEIRGHDEGSSLEEPLIESSEV

ADNRKVQELQGEGGIRLPNGERP**FHCNQCGASFTQKGNLLRHIKL

H**SGEKPFKCPFCSYACRRRDALTGHLRTHSVPPMEDCKEQEPIMD

NNISLVPFERPAVIEKLTGNMGKRKSSTPQKFVGEKLMRFSYPDI

HFDMNLTYEKEAELMQSHMMDQAINNAITYLGAEALHPLMQHPPS

TIAEVAPVISSAYSQVYHPNRIERPISRETADSHENNMDGPISLI

RPKSRPQEREASPSNSCLDSTDSESSHDDHQSYQGHPALNPKRKQ

SPAYMKEDVKALDTTKAPKGSLKDIYKVFNGEGEQIRAFKCEHCR

VLFLDHVMYTIHMGCHGYRDPLECNICGYRSQDRY EFSSHIVRG

EHTFH
```

The "Helios" isoforms 1, 2, 4, 6, and 7 listed above includes the degron FHCNQCGASFTQKGNLLRHIKLH (SEQ ID NO: 23). A degron is a portion of a protein that plays a role in regulating protein degradation rates. Helios protein also includes isoforms encoded by amino acid sequences Q9UKS7-3, Q9UKS7-5 and Q9UKS7-8.

As used herein, "Aiolos" protein is encoded by the IKZF3 gene. Aiolos protein is also known as IKAROS family zinc finger 3. ZNFN1A3, zinc finger protein, subfamily 1 A, 3, Ikaros family zinc finger protein 3, and AIO. Aiolos protein includes the following human isoforms listed below:

```
Isoform 1 (UniProt Q9UKT9-1)
                                          (SEQ ID NO: 12)
MEDIQTNAELKSTQEQSVPAESAAVLNDYSLTKSHEMENVDSGEG

PANEDEDIGDDSMKVKDEYSERDENVLKSEPMGNAEEPEIPYSYS

REYNEYENIKLERHVVSFDSSRPTSGKMNCDVCGLSCISFNVLMV

HKRSHTGERPFQCNQCGASFTQKGNLLRHIKLHTGEKPFKCHLCN

YACQRRDALTGHLRTHSVEKPYKCEFCGRSYKQRSSLEEHKERCR

TFLQSTDPGDTASAEARHIKAEMGSERALVLDRLASNVAKRKSSM

PQKFIGEKRHCFDVNYNSSYMYEKESELIQTRMMDQAINNAISYL

GAEALRPLVQTPPAPTSEMVPVISSMYPIALTRAEMSNGAPQELE

KKSIHLPEKSVPSERGLSPNNSGHDSTDTDSNHEERQNHIYQQNH

MVLSRARNGMPLLKEVPRSYELLKPPPICPRDSVKVINKEGEVMD

VYRCDHCRVLFLDYVMFTIHMGCHGFRDPFECNMCGYRSHDRYEF

SSHIARGEHRALLK

Isoform 3 (UniProt Q9UKT9-3)
                                          (SEQ ID NO: 13)
MEDIQTNAELKSTQEQSVPAESAAVLNDYSLTKSHEMENVDSGEG

PANEDEDIGDDSMKVKDEYSERDENVLKSEPMGNAEEPEIPYSYS

REYNEYENIKLERHVVSFDSSRPTSGKMNCDVCGLSCISFNVLMV

HKRSHTGERPFQCNQCGASFTQKGNLLRHIKLHTGEKPFKCHLCN

YACQRRDALTGHLRTHSASAEARHIKAEMGSERALVLDRLASNVA

KRKSSMPQKFIGEKRHCFDVNYNSSYMYEKESELIQTRMMDQAIN

NAISYLGAEALRPLVQTPPAPTSEMVPVISSMYPIALTRAEMSNG

APQELEKKSIHLPEKSVPSERGLSPNNSGHDSTDTDSNHEERQNH

IYQQNHMVLSRARNGMPLLKEVPRSYELLKPPPICPRDSVKVINK

EGEVMDVYRCDHCRVLFLDYVMFTIHMGCHGFRDPFECNMCGYRS

HDRYEFSSHIARGEHRALLK

Isoform 4 (UniProt Q9UKT9-4)
                                          (SEQ ID NO: 14)
MEDIQTNAELKSTQEQSVPAESAAVLNDYSLTKSHEMENVDSGEG

PANEDEDIGDDSMKVKDEYSERDENVLKSEPMGNAEEPEIPYSYS

REYNEYENIKLERHVVSFDSSRPTSGKMNCDVCGLSCISFNVLMV

HKRSHTGERPFQCNQCGASFTQKGNLLRHIKLHTGEKPFKCHLCN

YACQRRDALTGHLRTHSVEKPYKCEFCGRSYKQRSSLEEHKERCR

TFLQSTDPGDTGEKRHCFDVNYNSSYMYEKESELIQTRMMDQAIN

NAISYLGAEALRPLVQTPPAPTSEMVPVISSMYPIALTRAEMSNG

APQELEKKSIHLPEKSVPSERGLSPNNSGHDSTDTDSNHEERQNH

IYQQNHMVLSRARNGMPLLKEVPRSYELLKPPPICPRDSVKVINK

EGEVMDVYRCDHCRVLFLDYVMFTIHMGCHGFRDPFECNMCGYRS

HDRYEFSSHIARGEHRALLK

Isoform 6 (UniProt Q9UKT9-6)
                                          (SEQ ID NO: 15)
MEDIQTNAELKSTQEQSVPAESAAVLNDYSLIKSHEMENVDSGEG

PANEDEDIGDDSMKVKDEYSERDENVLKSEPMGNAEEPEIPYSYS

REYNEYENIKLERHVVSFDSSRPTSGKMNCDVCGLSCISFNVLMV

HKRSHTGERPFQCNQCGASFTQKGNLLRHIKLHTGEKPFKCHLCN

YACQRRDALTGHLRTHSGEKRHCFDVNYNSSYMYEKESELIQTRM

MDQAINNAISYLGAEALRPLVQTPPAPTSEMVPVISSMYPIALTR

AEMSNGAPQELEKKSIHLPEKSVPSERGLSPNNSGHDSTDTDSNH

EERQNHIYQQNHMVLSRARNGMPLLKEVPRSYELLKPPPICPRDS

VKVINKEGEVMDVYRCDHCRVLFLDYVMFTIHMGCHGFRDPFECN

MCGYRSHDRYEFSSHIARGEHRALLK

Isoform 7 (UniProt Q9UKT9-7)
                                          (SEQ ID NO: 16)
MEDIQTNAELKSTQEQSVPADDSMKVKDEYSERDENVLKSEPMGN

AEEPEIPYSYSREYNEYENIKLERHVVSFDSSRPTSGKMNCDVCG

LSCISFNVLMVHKRSHTGERPFQCNQCGASFTQKGNLLRHIKLHT

GEKPFKCHLCNYACQRRDALTGHLRTHSVEKPYKCEFCGRSYKQR

SSLEEHKERCRTFLQSTDPGDTASAEARHIKAEMGSERALVLDRL

ASNVAKRKSSMPQKFIGEKRHCFDVNYNSSYMYEKESELIQTRMM

DQAINNAISYLGAEALRPLVQTPPAPTSEMVPVISSMYPIALTRA

EMSNGAPQELEKKSIHLPEKSVPSERGLSPNNSGHDSTDTDSNHE

ERQNHIYQQNHMVLSRARNGMPLLKEVPRSYELLKPPPICPRDSV

KVINKEGEVMDVYRCDHCRVLFLDYVMFTIHMGCHGFRDPFECNM

CGYRSHDRYEFSSHIARGEHRALLK

Isoform 8 (UniProt Q9UKT9-8)
                                          (SEQ ID NO: 17)
MEDIQTNAELKSTQEQSVPADDSMKVKDEYSERDENVLKSEPMGN

AEEPEIPYSYSREYNEYENIKLERHVVSFDSSRPTSGKMNCDVCG

LSCISFNVLMVHKRSHTGERPFQCNQCGASFTQKGNLLRHIKLHT

GEKPFKCHLCNYACQRRDALTGHLRTHSASAEARHIKAEMGSERA

LVLDRLASNVAKRKSSMPQKFIGEKRHCFDVNYNSSYMYEKESEL

IQTRMMDQAINNAISYLGAEALRPLVQTPPAPTSEMVPVISSMYP

IALTRAEMSNGAPQELEKKSIHLPEKSVPSERGLSPNNSGHDSTD

TDSNHEERQNHIYQQNHMVLSRARNGMPLLKEVPRSYELLKPPPI

CPRDSVKVINKEGEVMDVYRCDHCRVLFLDYVMFTIHMGCHGFRD

PFECNMCGYRSHDRYEFSSHIARGEHRALLK

Isoform 9 (UniProt Q9UKT9-9)
                                          (SEQ ID NO: 18)
MEDIQTNAELKSTQEQSVPAESAAVLNDYSLTKSHEMENVDSGEG

PANEDEDIGGERPFQCNQCGASFTQKGNLLRHIKLHTGEKPFKCH

LCNYACQRRDALTGHLRTHSVEKPYKCEFCGRSYKQRSSLEEHKE

RCRTFLQSTDPGDTASAEARHIKAEMGSERALVLDRLASNVAKRK
```

```
SSMPQKFIGEKRHCFDVNYNSSYMYEKESELIQTRMMDQAINNAI

SYLGAEALRPLVQTPPAPTSEMVPVISSMYPIALTRAEMSNGAPQ

ELEKKSIHLPEKSVPSERGLSPNNSGHDSTDTDSNHEERQNHIYQ

QNHMVLSRARNGMPLLKEVPRSYELLKPPPICPRDSVKVINKEGE

VMDVYRCDHCRVLFLDYVMFTIHMGCHGFRDPFECNMCGYRSHDR

YEFSSHIARGEHRALLK

Isoform 14 (UniProt Q9UKT9-14)
                                    (SEQ ID NO: 19)
MEDIQTNAELKSTQEQSVPAESAAVLNDYSLTKSHEMENVDSGEG

PANEDEDIGDDSMKVKDEYSERDENVLKSEPMGNAEEPEIPYSYS

REYNEYENIKLERHVVSFDSSRPTSGKMNCDVCGLSCISFNVLMV

HKRSHTGERPFQCNQCGASFTQKGNLLRHIKLHTGEKPFKCHLCN

YACQRRDALTGHLRTHSVEKPYKCEFCGRSYKQRSSLEEHKERCR

TFLQSTDPGDTGTGWGWVELSHLGIRLQDLNVPWCRLH
```

The "Aiolos" protein isoforms 1, 3, 4, 6, 7, 8, 9, and 14 listed above includes the degron FQCNQCGASFTQKGNLLRHIKLH (SEQ ID NO: 24), which is the same as the degron for the "Ikaros" protein. Aiolos protein also includes isoforms encoded by amino acid sequences Q9UKT9-2, Q9UKT9-5, Q9UKT9-10, Q9UKT9-11, Q9UKT9-12, and Q9UKT9-13, Q9UKT9-15, and Q9UKT9-16.

As used herein, "Eos" protein is encoded by the IKZF4 gene and is also known as IKAROS family zinc finger 4, ZNFN1A4, zinc finger protein, subfamily IA, 4, Ikaros family zinc finger protein 4, and KIAA1782. "Eos" protein includes isoforms encoded by the following two human isoforms 1 (Q9H2S9-1) and 2 (Q9H2S9-2):

```
Isoform 1 (UniProt Q9H2S9-1)
                                    (SEQ ID NO: 20)
MHTPPALPRRFQGGGRVRTPGSHRQGKDNLERDPSGGCVPDFLPQ

AQDSNHFIMESLFCESSGDSSLEKEFLGAPVGPSVSTPNSQHSSP

SRSLSANSIKVEMYSDEESSRLLGPDERLLEKDDSVIVEDSLSEP

LGYCDGSGPEPHSPGGIRLPNGKLKCDVCGMVCIGPNVLMVHKRS

HTGERPFHCNQCGASFTQKGNLLRHIKLHSGEKPFKCPFCNYACR

RRDALTGHLRTHSVSSPTVGKPYKCNYCGRSYKQQSTLEEHKERC

HNYLQSLSTEAQALAGQPGDEIRDLEMVPDSMLHSSSERPTFIDR

LANSLTKRKRSTPQKFVGEKQMRFSLSDLPYDVNSGGYEKDVELV

AHHSLEPGFGSSLAFVGAEHLRPLRLPPTNCISELTPVISSVYTQ

MQPLPGRLELPGSREAGEGPEDLADGGPLLYRPRGPLTDPGASPS

NGCQDSTDTESNHEDRVAGWSLPQGPPPQPPPTIWGRHSPAYAKE

DPKPQEGLLRGTPGPSKEVLRWGESGEPVKAFKCEHCRILFLDHV

MFTIHMGCHGFRDPFECNICGYHSQDRYEFSSHIVRGEHKVG

Isoform 2 (UniProt Q9H2S9-2)
                                    (SEQ ID NO: 21)
MDSRYLQLQLYLPSCSLLQGSGDSSLEKEFLGAPVGPSVSTPNSQ

HSSPSRSLSANSIKVEMYSDEESSRLLGPDERLLEKDDSVIVEDS

LSEPLGYCDGSGPEPHSPGGIRLPNGKLKCDVCGMVCIGPNVLMV

HKRSHTGERPFHCNQCGASFTQKGNLLRHIKLHSGEKPFKCPFCN

YACRRRDALTGHLRTHSVSSPTVGKPYKCNYCGRSYKQQSTLEEH

KERCHNYLQSLSTEAQALAGQPGDEIRDLEMVPDSMLHSSSERPT

FIDRLANSLTKRKRSTPQKFVGEKQMRFSLSDLPYDVNSGGYEKD

VELVAHHSLEPGFGSSLAFVGAEHLRPLRLPPTNCISELTPVISS

VYTQMQPLPGRLELPGSREAGEGPEDLADGGPLLYRPRGPLTDPG

ASPSNGCQDSTDTESNHEDRVAGWSLPQGPPPQPPPTIWGRHSPA

YAKEDPKPQEGLLRGTPGPSKEVLRWGESGEPVKAFKCEHCRILF

LDHVMFTIHMGCHGFRDPFECNICGYHSQDRYEFSSHIVRGEHKV

G
```

The "Eos" protein isoforms 1 and 2 listed above includes the degron FHCNQCGASFTQKGNLLRHIKLH (SEQ ID NO: 25), which is the same as the degron for the "Helios" protein.

As used herein, "Pegasus" protein is also known as IKAROS family zinc finger 5, ZNFN1A5, zinc finger protein, subfamily IA, 5, and Ikaros family zinc finger protein 5. Pegasus is encoded by the IKZF5 gene.

As used herein, the term "contacting" refers to the bringing together of indicated moieties in an in vitro system or an in vivo system. For example, "contacting" IKZF1-4 proteins with a compound of Formula (I) includes the administration of a compound of the present invention to an individual or patient, such as a human, having Ikaros protein, Helios protein, Aiolos protein, and Eos protein as well as, for example, introducing a compound of Formula (I) into a sample containing a cellular or purified preparation containing Ikaros protein, Helios protein, Aiolos protein, and Eos protein.

The terms "treat," "treating." and "treatment." as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. In contrast, "prophylaxis" or "prevention" refers to administration to a subject who does not have a disease to prevent the disease from occurring. "Treat," "treating," and "treatment" does not encompass prophylaxis or prevention.

"Therapeutically effective amount" is intended to include an amount of a compound of the present invention alone or an amount of a compound of the present invention in combination with other active ingredients effective to decrease the levels of the IKZF1-4 proteins in the cells, or effective to treat or prevent viral infections and proliferative disorders, such as cancer.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

The term "patient" includes human subjects.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising the compound of the invention in combination with at least one additional pharmaceutically acceptable carrier.

UTILITY

The compounds of Formula (I) are useful for the treatment of cancer.

The compounds of Formula (I) are useful for the treatment of a viral infection.

In one embodiment, a method is provided for the treatment of cancer in a patient comprising administering to said patient a therapeutically effective amount of a compound according to Formula (I), or a stereoisomer, a tautomer, or a pharmaceutically acceptable salt thereof.

In one embodiment, a method is provided for the treatment of a viral infection in a patient comprising administering to said patient a therapeutically effective amount of a compound according to Formula (I), or a stereoisomer, a tautomer, or a pharmaceutically acceptable salt thereof.

In one embodiment, a method is provided for the treatment of cancer, in a patient comprising administering to said patient a therapeutically effective amount of a compound having the structure:

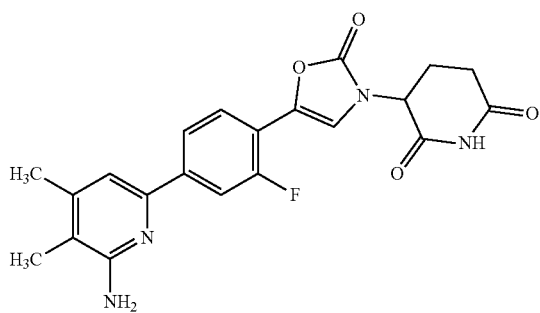 [SMILES: Cc1cc(-c2ccc(-c3cn(C4CCC(=O)NC4=O)c(=O)o3)c(F)c2)nc(N)c1C]

or a stereoisomer, a tautomer, or a pharmaceutically acceptable salt thereof.

One aspect provides a method of treating a disease or disorder by decreasing the levels of the four IKZF1-4 proteins Ikaros, Helios, Aiolos, and Eos, the method comprising administering to a patient a therapeutically effective amount of an agent to decrease the Ikaros, Helios, Aiolos, and Eos protein levels. In one embodiment, the disease or disorder is cancer. In another embodiment, the disease or disorder is a viral infection. In an additional embodiment, the agent is a compound of Formula (I), a stereoisomer, a tautomer, or a pharmaceutically acceptable salt thereof.

In one embodiment, a method is provided for the treatment of a disease or disorder in a patient comprising administering to said patient a therapeutically effective amount of an agent to decrease the Ikaros, Helios, Aiolos, and Eos protein levels, wherein: a) said Ikaros protein is the amino acid sequence encoded by SEQ ID NOs: 1, 2, 3, 4, 5, or 6; b) said Helios protein is the amino acid sequence encoded by SEQ ID NOs: 7,8, 9, 10, or 11; c) said Aiolos protein is the amino acid sequence encoded by SEQ ID NOs: 12, 13, 14, 15, 16, 17, 18, or 19; and d) said Eos protein is the amino acid sequence encoded by SEQ ID NOs: 20 or 21.

In Embodiment 1, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 30%; (ii) said Helios (IKZF2) protein level is decreased by at least 50%; (iii) said Aiolos (IKZF3) protein level is decreased by at least 30%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 2, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 40%; (ii) said Helios (IKZF2) protein level is decreased by at least 50%; (iii) said Aiolos (IKZF3) protein level is decreased by at least 40%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 3, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 50%; (ii) said Helios (IKZF2) protein level is decreased by at least 50%; (iii) said Aiolos (IKZF3) protein level is decreased by at least 50%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 4, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%; (ii) said Helios (IKZF2) protein level is decreased by at least 50%; (iii) said Aiolos (IKZF3) protein level is decreased by at least 60%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 5, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 30%, (ii) said Helios (IKZF2) protein level is decreased by at least 60%; (iii) said Aiolos (IKZF3) protein level is decreased by at least 30%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 6, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased by at least 40%; (ii) said Helios (IKZF2) protein level is decreased by at least 60%; (iii) said Aiolos (IKZF3) protein level is decreased by at least 40%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 7, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased by at least 50%; (ii) said Helios (IKZF2) protein level is decreased by at least 60%; (iii) said Aiolos (IKZF3) protein level is decreased by at least 50%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 8, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%; (ii) said Helios (IKZF2) protein level is decreased by at least 60%; (iii) said Aiolos (IKZF3) protein level is decreased by at least 60%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 9, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 30%; (ii) said Helios (IKZF2) protein level is decreased by at least 70%; (iii) said Aiolos (IKZF3) protein level is decreased by at least 30%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 10, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 40%; (ii) said Helios (IKZF2) protein level is deceased by at least 70%: (iii) said Aiolos (IKZF3) protein level is decreased by at least 40%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 11, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased by at least 50%; (ii) said Helios (IKZF2) protein level is decreased by at least 70%: (iii) said Aiolos (IKZF3) protein level is decreased by at least 50%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 12, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%: (ii) said Helios (IKZF2) protein level is decreased by at least 70%: (iii) said Aiolos (IKZF3) protein level is decreased by at least 60%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 13, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 30%; (ii) said Helios (IKZF2) protein level is decreased by at least 80%; (iii) said Aiolos (IKZF3) protein level is decreased by at least 30%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 14, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 40%; (ii) said Helios (IKZF2) protein level is decreased by at least 80%; (iii) said Aiolos (IKZF3) protein level is decreased by at least 40%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 15, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 50%; (ii) said Helios (IKZF2) protein level is decreased by at least 80%; (iii) said Aiolos (IKZF3) protein level is decreased by at least 50%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 16, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%; (ii) said Helios (IKZF2) protein level is decreased by at least 80%; (iii) said Aiolos (IKZF3) protein level is decreased by at least 60%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 17, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased by at least 30%; (ii) said Helios (IKZF2) protein level is decreased by at least 85%; (iii) said Aiolos (IKZF3) protein level is decreased by at least 30%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 18, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 40%; (ii) said Helios (IKZF2) protein level is decreased by at least 85%; (iii) said Aiolos (IKZF3) protein level is decreased by at least 40%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 19, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased by at least 50%; (ii) said Helios (IKZF2) protein level is decreased by at least 85%; (iii) said Aiolos (IKZF3) protein level is decreased by at least 50%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 20, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%; (ii) said Helios (IKZF2) protein level is decreased by at least 85%; (iii) said Aiolos (IKZF3) protein level is decreased by at least 60%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 21, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased by at least 30%; (ii) said Helios (IKZF2) protein level is decreased by at least 90%; (iii) said Aiolos (IKZF3) protein level is decreased by at least 30%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 22, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased by at least 40%; (ii) said Helios (IKZF2) protein level is decreased by at least 90%: (iii) said Aiolos (IKZF3)

protein level is decreased by at least 40%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 23, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 50%: (ii) said Helios (IKZF2) protein level is decreased by at least 90%: (iii) said Aiolos (IKZF3) protein level is decreased by at least 50%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 24, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 60%; (ii) said Helios (IKZF2) protein level is decreased by at least 90%: (iii) said Aiolos (IKZF3) protein level is decreased by at least 60%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 25, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 30%; (ii) said Helios (IKZF2) protein level is decreased by at least 90%; (iii) said Aiolos (IKZF3) protein level is decreased by at least 30%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 26, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased by at least 40%; (ii) said Helios (IKZF2) protein level is decreased by at least 90%; (iii) said Aiolos (IKZF3) protein level is decreased by at least 40%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 27, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased by at least 50%; (ii) said Helios (IKZF2) protein level is decreased by at least 90%; (iii) said Aiolos (IKZF3) protein level is decreased by at least 50%, and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 28, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased by at least 60%; (ii) said Helios (IKZF2) protein level is decreased by at least 90%; (iii) said Aiolos (IKZF3) protein level is decreased by at least 60%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 29, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 40 to 70%: (ii) said Helios (IKZF2) protein level is decreased by at least 50%; (iii) said Aiolos (IKZF3) protein level is decreased in the range of 40 to 70%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 30, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 40 to 70%; (ii) said Helios (IKZF2) protein level is decreased by at least 60%; (iii) said Aiolos (IKZF3) protein level is decreased in the range of 40 to 70%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 31, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 40 to 70%; (ii) said Helios (IKZF2) protein level is decreased by at least 70%: (iii) said Aiolos (IKZF3) protein level is decreased in the range of 40 to 70%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 32, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased in the range of 40 to 70%; (ii) said Helios (IKZF2) protein level is decreased by at least 70%: (iii) said Aiolos (IKZF3) protein level is decreased in the range of 40 to 70%; and (iv) said Eos (IKZF4) protein level is decreased by at least 70%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 33, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 40 to 70%; (ii) said Helios (IKZF2) protein level is decreased by at least 80%: (iii) said Aiolos (IKZF3) protein level is decreased in the range of 40 to 70%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 34, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 40 to 70%; (ii) said Helios (IKZF2) protein level is decreased by at least 90%; (iii) said Aiolos (IKZF3) protein level is decreased in the range of 40 to 70%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 35, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 50 to 70%; (ii) said Helios (IKZF2) protein level is decreased by at least 50%; (iii) said Aiolos (IKZF3) protein level is decreased in the range of 50 to 70%; and (iv) said Eos (IKZF4) protein level is decreased by at least 50%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 36, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 50 to 70%; (ii) said Helios (IKZF2) protein level is decreased by at least 60%; (iii) said Aiolos (IKZF3) protein level is decreased in the range of 50 to 70%; and (iv) said Eos (IKZF4) protein level is decreased by at least 60%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 37, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF1) protein level is decreased in the range of 50 to 70%: (ii) said Helios (IKZF2) protein level is decreased by at least 70%: (iii) said Aiolos (IKZF3) protein level is decreased in the range of 50 to 70%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 38, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased in the range of 50 to 70%; (ii) said Helios (IKZF2) protein level is decreased by at least 70%; (iii) said Aiolos (IKZF3) protein level is decreased in the range of 50 to 70%; and (iv) said Eos (IKZF4) protein level is decreased by at least 70%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 39, a method is provided for the treatment of disease or disorder in a patient comprising administering to said patient a therapeutically effective amount of an agent to decrease the Ikaros, Helios, Aiolos, and Eos protein levels, wherein: (i) said Ikaros (IKZF 1) protein level is decreased in the range of 50 to 70%; (ii) said Helios (IKZF2) protein level is decreased by at least 80%; (iii) said Aiolos (IKZF3) protein level is decreased in the range of 50 to 70%; and (iv) said Eos (IKZF4) protein level is decreased by at least 65%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiment 40, a method is provided for the treatment of disease or disorder in a patient comprising administering to said patient a therapeutically effective amount of an agent to decrease the Ikaros. Helios, Aiolos, and Eos protein levels, wherein: (i) said Ikaros (IKZF1) protein level is decreased in the range of 50 to 70%; (ii) said Helios (IKZF2) protein level is decreased by at least 90%; (iii) said Aiolos (IKZF3) protein level is decreased in the range of 50 to 70%; and (iv) said Eos (IKZF4) protein level is decreased by at least 90%. Included in this embodiment is a method where the disease or disorder is cancer. Also included in this embodiment is a method wherein the disease or disorder is a viral infection. Additionally, included in this embodiment is a method wherein the agent is a compound of Formula (I), a stereoisomer, a tautomer, or a pharmaceutically acceptable salt thereof.

In Embodiments 1 to 40, the decreases in the protein levels of the IKZF1-4 proteins can be measured using the following assays described hereinbelow: (i) IKZF1: Human $CD8^+$ T Cell Reprogramming Assay: (ii) IKZF2: Jurkat Cellular Degradation Assay; (iii) IKZF3: Human $CD8^+$ T Cell Reprogramming Assay; and (iv) IKZF4: Human T Regulatory Cell Reprogramming Assay.

Types of cancers that may be treated with the compounds of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma. Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is melanoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is lung cancer, including small cell lung cancer (SCLC) and non-small cell lung cancer (NSCLC).

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is mesothelioma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is breast cancer, including ductal carcinoma, invasive ductal carcinoma metastatic breast cancer, triple negative breast cancer, human epidermal growth factor receptor 2 (HER2) positive breast cancer, estrogen receptor (ER) positive breast cancer, hormone receptor-positive breast cancer, and hormone-receptor negative breast cancer.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is prostate cancer, including adenocarcinoma of the prostate and castration-resistant prostate cancer.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is pancreatic cancer, including pancreatic adenocarcinoma, exocrine pancreatic cancer and neuroendocrine pancreatic cancer.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is kidney cancer, including renal cell carcinoma, clear cell renal cell carcinoma, and non-clear cell renal cell carcinomas, papillary renal cell carcinoma, Wilms tumor, and renal sarcoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is gastric cancer, including gastric carcinoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is kidney cancer, including renal carcinoma and kidney parenchymal carcinoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is liver cancer, including hepatocellular carcinoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is ovarian cancer, including ovarian carcinoma.

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is lymphoma, including Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia, and diffuse large B-cell lymphoma (DLBCL).

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is leukemia, including acute lymphatic leukemia (ALL), chronic lymphatic leukemia (CLL), acute myeloid leukemia (AML), chronic myeloid leukemia (CML), adult T-cell leukemia lymphoma, and diffuse large B-cell lymphoma (DLBCL).

In one embodiment, a method is provided for the treatment of cancer, in a patient comprising administering to said patient a therapeutically effective amount of the compound according to Formula (I), or a stereoisomer, a tautomer, or a pharmaceutically acceptable salt thereof, wherein said cancer is multiple myeloma.

The compounds for Formula (I) and pharmaceutical compositions comprising a compound of Formula (I) are useful in treating or preventing any diseases or conditions that are associated with the activity of IKZF1-4 proteins. These include viral and other infections (e.g., skin infections, GI infection, urinary tract infections, genito-urinary infections, systemic infections), and proliferative diseases (e.g., cancer). Any method of administration may be used to deliver the compound or pharmaceutical composition to the patient. In certain embodiments, the compounds of Formula (I) or pharmaceutical composition comprising a compound of Formula (I) are administered orally. In other embodiments, the compounds of Formula (I) or pharmaceutical composition comprising a compound of Formula (I) are administered parenterally.

In one embodiment, a method is provided for the treatment of a viral infection in a patient comprising administering to said patient a therapeutically effective amount of the compound according to Formula (I), or a stereoisomer, a tautomer, or a pharmaceutically acceptable salt thereof, wherein said viral infection is caused by exposure to HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The compounds of Formula (I) can selectively decrease the protein levels of the four IKZF1-4 proteins in cells to control Treg differentiation. For example, the compounds of Formula (I) can be used to selectively decrease the protein level, decrease the activity level and/or inhibit the expression level of each of the four IKZF1-4 proteins in the cells to control Treg differentiation in a cell or in an individual in need of a decrease in the protein level, decrease in the activity level and/or inhibition of the expression level of each of the four IKZF1-4 proteins by administering an efficacious amount of the compounds of Formula (I) or a stereoisomer, a tautomer, or a salt thereof.

In one embodiment, the present invention provides a combined preparation of the compounds of Formula (I), and/or a pharmaceutically acceptable salt thereof; and additional therapeutic agent(s) for simultaneous, separate or sequential use in the treatment and/or prophylaxis of multiple diseases or disorders associated with the activity of IKZF1-4 proteins. The combined preparation can be used to decrease the protein level, to decrease the protein activity level, and/or to inhibit the expression level of each of the four IKZF1-4 proteins.

In one aspect, a compound of Formula (I) is sequentially administered prior to administration of the immuno-oncology agent. In another aspect, a compound of Formula (I) is administered concurrently with the immuno-oncology agent. In yet another aspect, a compound of Formula (I) is sequentially administered after administration of the immuno-oncology agent.

In another aspect, a compound of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PDIH, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with a compound of Formula (I) for the treatment of cancer include antagonists of inhibitory receptors on NK cells or agonists of activating receptors on NK cells. For example, a compound of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, a compound of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO207/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO206/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with a compound of Formula (I) for treatment of IKZF1-4 proteins associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with a compound of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. A compound of Formula (I) may also be combined with immunotherapy drugs, including cytokines such as interferon alpha, interleukin 2, and tumor necrosis factor (TNF) in the treatment of melanoma.

The compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including a compound of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually, the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme: a topoisomerase inhibitor; procarbazine; mitoxantrone; platinum coordination complexes such as cisplatin and carboplatin; biological response modifiers: growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (200)); (v) cell cycle kinase inhibitors such as, for example, flavopiridol and UCN-O1 (see, for example, Sausville, *Curr. Med. Chem. Anti-Canc. Agents*, 3:47-56 (203)); and (vi) phosphatidyl inositol kinase inhibitors such as, for example, LY294002 (see, for example, Vlahos et al., *J Biol. Chem.*, 269:5241-5248 (1994)). Alternatively, at least one STI and a compound of Formula (I) may be in separate pharmaceutical compositions. In a specific embodiment of the present invention, a compound of Formula (I) and at least one STI may be administered to the patient concurrently or sequentially. In other words, at a compound of Formula (I) may be administered first, at least one STI may be administered first, or a compound of Formula (I) and at least one STI may be administered at the same time. Additionally, when a compound of Formula (I) and more than one STI is used, the compounds may be administered in any order.

The present invention further provides a pharmaceutical composition for the treatment of a chronic viral infection in a patient comprising a compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, a compound of Formula (I) and at least one chemotherapeutic agent are administered to the patient concurrently or sequentially. In other words, a compound of Formula (I) may be administered first, at least one chemotherapeutic agent may be administered first, or a compound of Formula (I) and the at least one STI may be administered at the same time. Additionally, when more than one chemotherapeutic agent is used, the compound and more than one chemotherapeutic agent may be administered in any order. Similarly, any antiviral agent or STI may also be administered at any point in comparison to the administration of a compound of Formula (I).

Chronic viral infections that may be treated using the present combinatorial treatment include, but are not limited to, diseases caused by hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV).

Suitable antiviral agents contemplated for use in combination with a compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549: MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959): ritonavir (ABT-538): indinavir (MK-639); nelfnavir (AG-1343): amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions

The invention also provides pharmaceutically compositions which comprise a therapeutically effective amount of a compound of Formula (I), formulated together with one or more pharmaceutically acceptable carriers (additives) and/or diluents, and optionally, one or more additional therapeutic agents described above.

The compounds of Formula (I) may be administered by any suitable route, preferably in the form of a pharmaceutical composition adapted to such a route, and in a dose effective for the treatment intended. The compound and compositions comprising a compound of Formula (I) can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors but can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing a compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water-soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing a compound of Formula (I) and/or at least one salt thereof with at least one inert solid diluent, such as, for example, calcium carbonate; calcium phosphate; and kaolin.

Soft gelatin capsules can, for example, be prepared by mixing a compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing a compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending a compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing a compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of a compound of Formula (I) and/or at least one pharmaceutically acceptable salt thereof can, for example, be prepared as an oil-in-water emulsion. The oily phase of the emulsions comprising a compound of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soybean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., Captisol), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving a compound of Formula (I) in an oily phase, such as, for example, a mixture of soybean oil and lecithin; 2) combining a compound of Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The amounts of the compound that is administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two-day cycle.

Pharmaceutical compositions of this invention comprise a compound of Formula (I) and/or at least one pharmaceutically acceptable salt thereof, and optionally an additional agent selected from any pharmaceutically acceptable carrier, adjuvant, and vehicle. Alternate compositions of this invention comprise the compound of the Formula (I) described herein, or a prodrug thereof, and a pharmaceutically acceptable carrier, adjuvant, or vehicle.

The present invention also includes pharmaceutical kits useful, for example, in the treatment or prevention of IKZF1-4 protein-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The dosage regimen for the compounds of the present invention will, of course, vary depending upon known factors, such as the pharmacodynamic characteristics of the particular agent and its mode and route of administration; the species, age, sex, health, medical condition, and weight of the recipient: the nature and extent of the symptoms; the kind of concurrent treatment: the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. A compound of Formula (I) may be administered in a single daily dose, or the total daily dosage may be administered in divided doses of two, three, or four times daily.

The compound is typically administered in an admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 200 milligrams of active ingredient per dosage unit. In these pharmaceutical compositions the active ingredient will ordinarily be present in an amount of about 0.1-95% by weight based on the total weight of the composition.

A typical capsule for oral administration contains a compound of Formula (I) (250 mg), lactose (75 mg), and magnesium stearate (15 mg). The mixture is passed through a 60-mesh sieve and packed into a No. 1 gelatin capsule.

A typical injectable preparation is produced by aseptically placing a compound of Formula (I) (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of a compound of Formula (I), alone or in combination with a pharmaceutical carrier. Optionally, a compound of Formula (I) can be used in combination with one or more other therapeutic agent(s), e.g., an anticancer agent or other pharmaceutically active material.

Regardless of the route of administration selected, a compound of Formula (I), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the therapeutic response for a particular patient, composition, and mode of administration, without being toxic to the patient.

The selected dosage level will depend upon a variety of factors including the activity of a compound of Formula (I) employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound of Formula (I) employed in the pharmaceutical composition at levels lower than that required in order to achieve the therapeutic effect and gradually increase the dosage until the effect is achieved.

In general, a suitable daily dose of a compound of Formula (I) will be that amount of the compound which is the lowest dose effective to produce a therapeutic effect. Such an effective dose will generally depend upon the factors described above. Generally, oral, intravenous, intracerebroventricular and subcutaneous doses of a compound of Formula (I) for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of Formula (I) to be administered alone, it is preferable to administer the compound as a pharmaceutical formulation (composition).

The above other therapeutic agents, when employed in combination with a compound of Formula (I), may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compound of the present invention can be prepared in a number of ways well known to one skilled in the art of organic synthesis. The compound of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compound of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Fourth Edition, Wiley and Sons, 207).

EXAMPLES

The following examples illustrate the particular embodiments of the present invention and do not limit the scope of the present invention. Chemical abbreviations and symbols as well as scientific abbreviations and symbols have their usual and customary meanings unless otherwise specified. Additional abbreviations employed in the Examples section and elsewhere in this application are defined below. The compound of the Example and intermediates are identified by the example and step in which they were prepared (e.g., "1-A" denotes the Example 1, step A), or by the example only where the compound is the title compound of the example (for example. "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, case of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances, some functional groups in the outlined examples and claims may be replaced by well-known bioisosteric replacements known in the art, for example, replacement of a carboxylic acid group with a tetrazole or a phosphate moiety.

ABBREVIATIONS

ACN acetonitrile
BISPIN bis(pinacolato)diboron
CatacXium-PD-G3 Mesylate[(di(1-adamantyl)-n-butylphosphine)-2-(2'-amino-1,1'-biphenyl)]palladium (II)
CDI carbonyldiimidazole
DBU 1,8-diazabicyclo[5.4.0]undec-7-ene
DCM dichloromethane
DIPEA N,N-diisopropylethylamine
DME dimethyl ether
DMF dimethylformamide
DMSO dimethyl sulfoxide
dppf bis(diphenylphosphino)ferrocene
EtOAc ethyl acetate
HPLC High Performance Liquid Chromatography
Me methyl
MeOH methanol
min minute(s)
mL milliliter(s)
NCS N-chlorosuccinimide
NH$_4$OAc ammonium acetate
NMP N-methylpyrrolidinone
Pd(dppf)$_2$Cl$_2$ [1,1'-his(diphenylphosphino)ferrocene]dichloropalladium(II)

SEM-Cl 2-trimethylsilyl)ethoxymethyl chloride
TEA triethylamine
TFA trifluoroacetic acid
THF tetrahydrofuran Analytical LCMS Conditions Method A: ACQUITY UPLC® BEH C18 (3.0×50 mm) 1.7 μm; Mobile Phase A: 95:5 water:acetonitrile with 2.5 mM NH$_4$OAc; Mobile Phase B: 5:95 water:acetonitrile with 2.5 mM NH$_4$O Ac; Temperature: 40° C.; Gradient: 20% B to 100% B over 2 min; flow: 0.7 mL/min; Detection: MS and UV (220 nm).

Method B: Column-Kinetex XB-C18 (75×3 mm-2.6 μm); Mobile Phase A: 10 mM NH$_4$COOH in water; Mobile Phase B: Acetonitrile: Gradient: 20% B to 100% B over 4.6 min, Flow: 1.0 mL/min.

Method C: Column: Waters Acquity BEH C18 1.7 μm 2.1×50 mm; Start % B: 0. Final % B: 100: Gradient Time: 1.0 min; Stop Time: 1.50 min; Flow Rate: 1.0 mL/min; Solvent A: A2=0.05% TFA in CH$_3$CN:Water (5:95); Solvent B: B2=0.05% TFA in CH$_3$CN:Water (95:5); Oven Temperature: 50° C.

Intermediate A 3-(5-(2-Fluoro-4-(4,4,5,5-tetramethyl-1,3,2-dioxaborolan-2-yl)phenyl)-2-oxoooxazol-3(2H)-yl)-1-((2-(trimethylsilyl)ethoxy)methyl)piperidine-2,6-dione

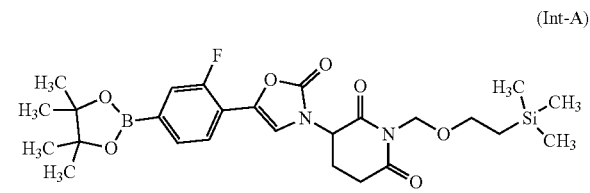

(Int-A)

Preparation of Intermediate A1:
2-bromo-1-(4-bromo-2-fluorophenyl)ethan-1-one

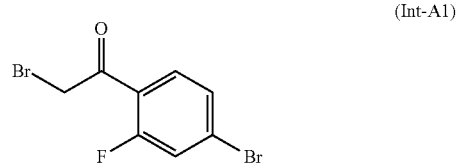 [SMILES: O=C(CBr)c1ccc(Br)cc1F]

(Int-A1)

To a stirred solution of 1-(4-bromo-2-fluorophenyl)ethan-1-one (44 g, 203 mmol) in EtOAc (1000 mL), was added copper(II) bromide (91 g, 405 mmol) at room temperature. The reaction mixture was heated at 60° C. for 16 h under argon, cooled to room temperature, and filtered through a celite pad. The filtrate was concentrated under vacuo. The crude product obtained was purified by flash chromatography (SiO$_2$, 330 g column, 0-10% EtOAc/pet ether) to afford 2-bromo-1-(4-bromo-2-fluorophenyl)ethan-1-one (32.8 g, 51%). $^1$H-NMR (400 MHz, CDCl$_3$): δ 4.50 (s, 2H), 7.40-7.48 (m, 2H), 7.83-7.87 (m, 1H).

Preparation of Intermediate A2: 3-((2-(4-bromo-2-fluorophenyl)-2-oxoethyl)amino)piperidine-2,6-dione

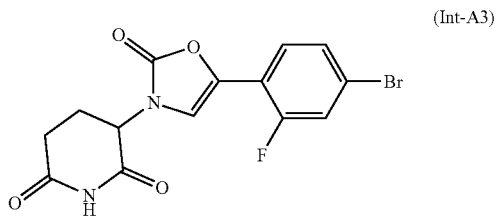 [SMILES: O=C1CCC(n2cc(-c3ccc(Br)cc3F)oc2=O)C(=O)N1]
(Int-A2)

To a stirred solution of 3-aminopiperidine-2,6-dione, HCl (22.25 g, 135 mmol) in THF (200 mL) was added K$_2$CO$_3$ (20 g, 145 mmol). The reaction mixture was stirred for 15 min under nitrogen, 2-Bromo-1-(4-bromo-2-fluorophenyl)ethan-1-one (20 g, 67.6 mmol) was added in portions and reaction mixture was heated at 70° C. for 2 h. The reaction mixture was cooled to room temperature, concentrated under vacuo and diluted with water (200 mL). The separated solid was filtered and dried under vacuo to afford 3-((2-(4-bromo-2-fluorophenyl)-2-oxoethyl)amino)piperidine-2,6-dione (19 g, 71%). LCMS (Method A): retention time 0.865 min, [M+H]$^+$ 344.0.

Preparation of Intermediate A3: 3-(5-(4-bromo-2-fluorophenyl)-2-oxooxazol-3(2H)-yl) piperidine2,6-dione (Int-A3)

To a stirred solution of 3-((2-(4-bromo-2-fluorophenyl)-2-oxoethyl)amino) piperidine-2,6-dione (30 g, 87 mmol) in THF (300 mL), were added K$_2$CO$_3$ (12.08 g, 87 mmol) and CDI (28.4 g, 175 mmol) at room temperature. The reaction mixture was stirred at the same temperature for 16 h, concentrated under vacuo and diluted with water (400 mL). The solid precipitate formed was filtered through Buchner funnel and dried under vacuo to afford 3-(5-(4-bromo-2-fluorophenyl)-2-oxooxazol-3(2H)-yl)piperidine-2,6-dione (21.1 g, 50%). LCMS (Method A): retention time 1.79 min, [M+H]$^+$ 370.0.

Preparation of Intermediate A4: 3-(5-(4-bromo-2-fluorophenyl)-2-oxooxazol-3(2H)-yl)-1-((2-(trimethylsilyl)ethoxy)methyl)piperidine-2,6-dione

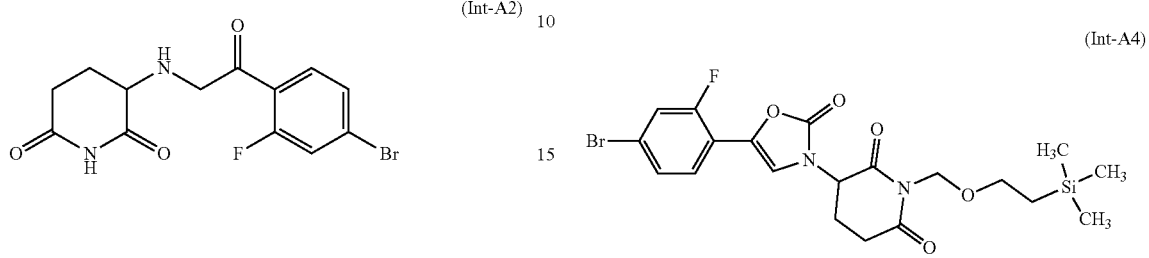
(Int-A4)

To a stirred solution of 3-(5-(4-bromo-2-fluorophenyl)-2-oxooxazol-3(2H)-yl) piperidine-2,6-dione (10 g, 27.1 mmol) in THF (100 mL), were added DBU (6.12 mL, 40.6 mmol) and SEM-Cl (5.77 mL, 32.5 mmol) at −50° C. under nitrogen. The reaction was continued at same temperature for 1 h and quenched with water. The reaction mixture was extracted with EtOAc (3×). The combined organic layer was washed with brine, dried over anhydrous sodium sulfate, filtered and concentrated under vacuo. The residue was purified by column chromatography (SiO$_2$, 0-60% EtOAc/pet ether) to afford 3-(5-(4-bromo-2-fluorophenyl)-2-oxooxazol-3(2H)-yl)-1-((2-(trimethylsilyl)ethoxy) methyl) piperidine-2,6-dione (6.2 g, 45%). LCMS (Method A): retention time 1.68 min, [M+H]$^+$ 500.1.

Preparation of Intermediate A

To a stirred solution of 3-(5-(4-bromo-2-fluorophenyl)-2-oxooxazol-3(2H)-yl)-1-((2-(trimethylsilyl)ethoxy)methyl) piperidine-2,6-dione (7 g, 14.0 mmol) in anhydrous 1,4 dioxane (70 mL) were added BISPIN (5.34 g, 21.02 mmol) and potassium acetate (1.651 g, 16.82 mmol) at room temperature. The reaction mixture was purged with argon for 10 min, Pd(dppf)C12.DCM complex (1.026 g, 1.40 mmol) was added under argon and the resulting mixture was heated for 1 h at 80° C. The reaction mixture was cooled to room temperature, diluted with EtOAc (70 mL), filtered through celite pad and the filtrate was concentrated under reduced pressure. The residue was purified by flash chromatography (SiO$_2$, 120 g column, 0-70% EtOAc/pet ether). Isolated product was stirred with diethyl ether for 1 h, filtered and dried under vacuo to afford 3-(5-(2-fluoro-4-(4,4,5,5-tetramethyl-1,3,2-dioxaborolan-2-yl)phenyl)-2-oxooxazol-3(2H)-yl)-1-((2-(trimethylsilyl) ethoxy)methyl) piperidine-2,6-dione (4.85 g, 63%) as a white solid. LCMS (Method A): retention time 2.16 min, [M−H]$^+$ 545.2; $^1$H NMR (CHLOROFORM-d, 300 MHz) δ 7.5-7.6 (m, 2H), 7.44 (d, 1H, J=11.7 Hz), 6.90 (d, 1H, J=2.3 Hz), 5.17 (d, 2H, J=12.5 Hz), 4.82 (dd, 1H, J=5.9, 12.7 Hz), 3.56 (t, 2H, J=8.1 Hz), 2.9-3.1 (m, 1H), 2.7-2.9 (m, 1H), 2.31 (br s, 2H), 1.28 (s, 12H), 0.8-0.9 (m, 2H), −0.07 (s, 9H).

Example 1

3-(5-(4-(6-Amino-4,5-dimethylpyridin-2-yl)-2-fluorophenyl)-2-oxooxazol-3(2H)-yl) piperidine-2,6-dione

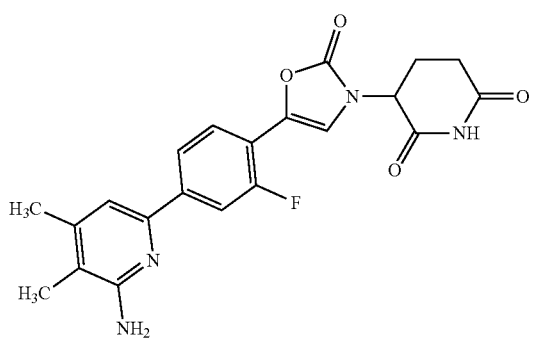

(I)

Preparation of Intermediate IA: 3-(5-(2-fluoro-4-(4,4,5,5-tetramethyl-1,3,2-dioxaborolan-2-yl)phenyl)-2-oxooxazol-3(2H)-yl)-1-((2-(trimethylsilyl)ethoxy)methyl)piperidine-2,6-dione

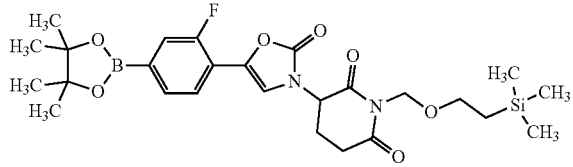

(1A)

To a vial, 6-chloro-3,4-dimethylpyridin-2-amine (1.24 g, 7.91 mmol), 3-(5-(2-fluoro-4-(4,4,5,5-tetramethyl-1,3,2-dioxaborolan-2-yl)phenyl)-2-oxooxazol-3(2H)-yl)-1-((2-(trimethylsilyl)ethoxy)methyl)piperidine-2,6-dione (Int-A, 3.93 g, 7.19 mmol), cesium carbonate (3.51 g, 10.79 mmol), dioxane (32 mL) and water (80 µL) were added at room temperature. The reaction mixture was purged with argon for 10 min, and CatacXium Pd G3 (0.157 g, 0.22 mmol) was added. The reaction mixture was heated at 100° C. for 8 h. The reaction mixture was cooled to room temperature, diluted with EtOAc and filtered through celite pad. The filtrate was washed with brine, dried over anhydrous Na₂SO₄, filtered and concentrated under reduced pressure. The residue was purified by flash chromatography (SiO₂, 80 g column, 0-4% MeOH/DCM) and the isolated product was recrystallized from EtOAc to afford 3-(5-(4-(6-amino-4,5-dimethylpyridin-2-yl)-2-fluorophenyl)-2-oxooxazol-3(2H)-yl)-1-((2-(trimethylsilyl) ethoxy)methyl)piperidine-2,6-dione (2.10 g, 54%) as a white solid. LCMS (Method A): retention time 1.86 min, [M+H]⁺ 541.3: ¹H NMR (CHLOROFORM-d, 300 MHz) δ 7.76 (br d, 2H, J=10.6 Hz), 7.6-7.7 (m, 1H), 6.9-7.0 (m, 2H), 5.2-5.3 (m, 2H), 4.89 (dd, 1H, J=6.0, 12.5 Hz), 4.46 (br s, 2H), 3.6-3.7 (m, 2H), 3.0-3.1 (m, 1H), 2.8-3.0 (m, 1H), 2.3-2.5 (m, 2H), 2.30 (s, 3H), 2.10 (s, 3H), 0.9-1.0 (m, 2H), 0.00 (s, 9H).

Preparation of Intermediate IB: 3-(5-(4-(6-amino-4,5-dimethylpyridin-2-yl)-2-fluorophenyl)-2-oxooxazol-3(2H)-yl)-1-(hydroxymethyl)piperidine-2,6-dione

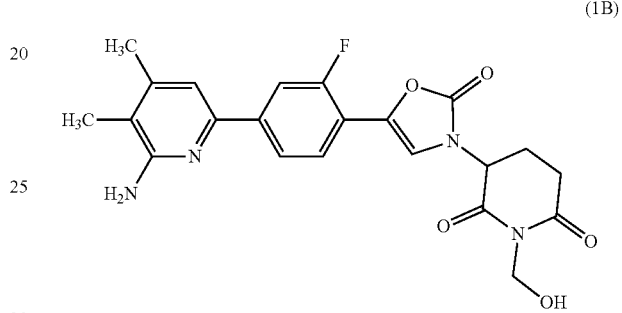

(1B)

To a stirred solution of 3-(5-(4-(6-amino-4,5-dimethylpyridin-2-yl)-2-fluorophenyl)-2-oxooxazol-3(2H)-yl)-1-((2-(trimethylsilyl)ethoxy)methyl)piperidine-2,6-dione (7.13 g, 13.18 mmol) in DCM (78 mL) was added TFA (20.3 mL, 264 mmol) at 0° C. The reaction mixture was warmed to room temperature, stirred for 1 h at room temperature, concentrated under reduced pressure, and co-evaporated with DME (4 times). LCMS (Method B): retention time 1.38 min, [M+H]⁺ 441.5.

Example 1

To a stirred solution of 3-(5-(4-(6-amino-4,5-dimethylpyridin-2-yl)-2-fluorophenyl)-2-oxooxazol-3(2H)-yl)-1-(hydroxymethyl)piperidine-2,6-dione (1.385 g, 3.14 mmol) in anhydrous DME (21 mL) was added N,N'-dimethylethylenediamine (1.692 mL, 15.7 mmol) at 0° C. under nitrogen. The reaction mixture was warmed to room temperature and stirred for 30 min. The reaction mixture was cooled to 0° C., acidified with acetic acid (1.8 mL, 31.4 mmol) and concentrated under reduced pressure (bath temp <30° C.). The residue was purified by flash chromatography (SiO₂, 40 g column, 0-6% MeOH/DCM) and the isolated product was recrystallized from EtOAc/diethyl ether to afford 3-(5-(4-(6-amino-4,5-dimethylpyridin-2-yl)-2-fluorophenyl)-2-oxooxazol-3(2H)-yl)piperidine-2,6-dione (0.48 g, 37%) as a white solid. LCMS (Method C): retention time 1.33 min, [M+H]⁺ 411.15; ¹H NMR (DMSO-d₆, 400 MHz) δ 11.13 (br s, 1H), 7.9-8.0 (m, 2H), 7.6-7.6 (m, 2H), 7.11 (s, 1H), 5.74 (s, 2H), 5.07 (dd, 1H, J=5.3, 13.0 Hz), 2.8-2.9 (m, 1H), 2.6-2.7 (m, 2H), 2.23 (s, 3H), 2.1-2.2 (m, 1H), 2.02 (s, 3H).

Example 2

3-(5-(4-(6-amino-4,5-dimethylpyridin-2-yl)-2-fluorophenyl)-2-oxooxazol-3(2H)-yl) piperidine-2,6-dione-3,4,4,5,5-D$_5$

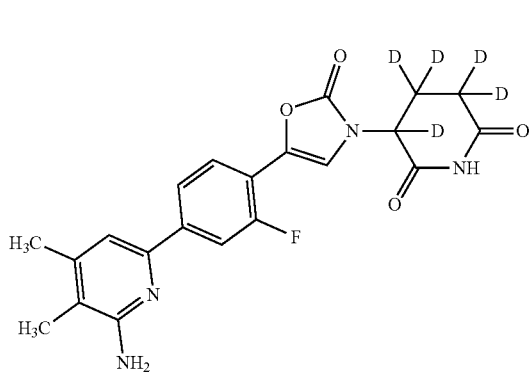

(2)

Preparation of Intermediate 2A: tert-butyl 4,5-diamino-5-oxopentanoate-2,2,3,3,4-D$_5$ hydrochloride

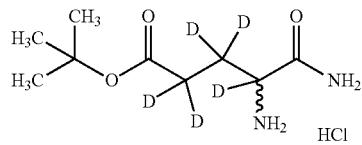

(2A)

tert-Butyl 4,5-diamino-5-oxopentanoate-2,2,3,3,4-D$_5$ hydrochloride was prepared according to the general method disclosed in WO2014116573 A1.

Preparation of Intermediate 2B: tert-butyl 5-amino-4-(5-(4-bromo-2-fluorophenyl)-2-oxooxazol-3(2H)-yl)-5-oxopentanoate-2,2,3,3,4-D$_5$

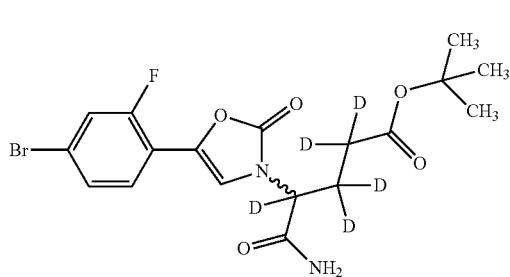

(2B)

To a 25 mL round bottom flask containing 2-bromo-1-(4-bromo-2-fluorophenyl) ethan-1-one (230 mg, 0.77 mmol) and tert-butyl 4,5-diamino-5-oxopentanoate-2,2,3,3,4-D$_5$ hydrochloride (208 mg, 0.86 mmol) in anhydrous DMF (2.4 mL), was added NaI (128 mg, 0.86 mmol). The reaction mixture was stirred at 0° C. for 10 min, then DIPEA was added dropwise at 0° C. (0.35 mL, 1.94 mmol). The reaction mixture was stirred at 0° C. for 3 hours. After 3 h, CDI (315 mg, 1.94 mmol) was added at 0° C., followed by dropwise addition of TEA (0.54 mL, 3.9 mmol). The reaction mixture was warmed up slowly to room temperature and stirred for 16 hours. The reaction mixture was diluted with EtOAc (7 mL) and H$_2$O (5 mL) and stirred at room temperature for 2 minutes. The organic layer was separated, and the water was back extracted with EtOAc (1×3 mL). The combined organic layer was concentrated to dryness and purified by ISCO (24 g Silica gel), eluted with 100% Hex—90% EtOAc/Hex: the product eluted at 40-45% EtOAc/Hex. The combined fractions containing the product were concentrated to dryness and dried overnight to afford tert-butyl 5-amino-4-(5-(4-bromo-2-fluorophenyl)-2-oxooxazol-3(2H)-yl)-5-oxopentanoate-2,2,3,3,4-D$_5$ as an orange solid (79 mg, 23% yield). LCMS (Method C): retention time 1.006 min, [M+H−Boc]$^+$ 391.8/393.7 (bromide isotopes).

Preparation of Intermediate 2C: tert-butyl 5-amino-4-(5-(2-fluoro-4-(4,4,5,5-tetramethyl-1,3,2-dioxaborolan-2-yl)phenyl)-2-oxooxazol-3(2H)-yl)-5-oxopentanoate-2,2,3,3,4-D$_5$

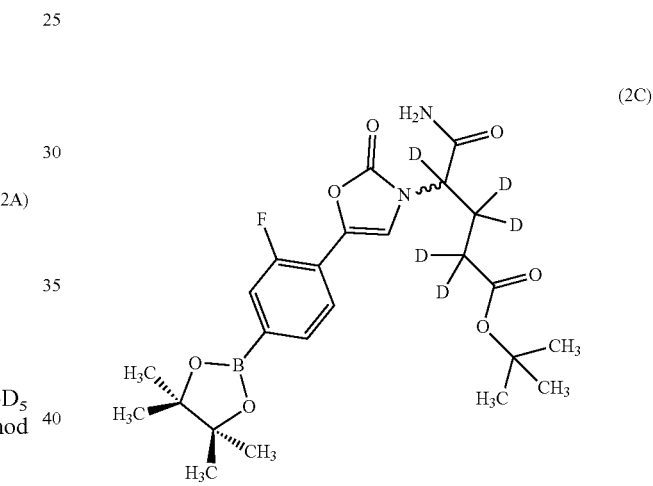

(2C)

To a stirred solution of tert-butyl 5-amino-4-(5-(4-bromo-2-fluorophenyl)-2-oxooxazol-3(2H)-yl)-5-oxopentanoate-2,2,3,3,4-D$_5$ (127 mg, 0.29 mmol) in 1,4-dioxane (2.5 ml) in a 10 mL-reactive vial that was degassed for 5 min with N$_2$, were added bis(pinacolato)diboron (108 mg, 0.43 mmol) and potassium acetate (56 mg, 0.57 mmol). The solution was purged under N$_2$ stream for 5 min, then 1,1'-bis(diphenylphosphino) ferrocenedichloro palladium(II) dichloromethane complex (21 mg, 0.029 mmol) was added. The solution was purged under nitrogen for another 5 min. The reaction mixture was heated at 80° C. for 16 hours. The reaction mixture was filtered through celite, then washed with EtOAc. The mother liquor was concentrated to dryness to afford a black oil. The crude residue was purified by ISCO (24 g Silica gel), eluted with 100% Hex to 80% EtOAc/Hex. The product eluted at 70% EtOAc/Hex. Combined fractions containing the product were concentrated to dryness and vacuum dried overnight to afford tert-butyl 5-amino-4-(5-(2-fluoro-4-(4,4,5,5-tetramethyl-1,3,2-dioxaborolan-2-yl) phenyl)-2-oxooxazol-3(2H)-yl)-5-oxopentanoate-2,2,3,3,4-D$_5$ as a brown foam (98 mg, 69% yield). LCMS (Method C): retention time 1.056 min, [M+H−Boc]$^+$ 439.8.

Preparation of Intermediate 2D: tert-butyl 5-amino-4-(5-(4-(6-(bis(tert-butoxycarbonyl)amino)-4,5-dimethylpyridin-2-yl)-2-fluorophenyl)-2-oxooxazol-3(2H)-yl)-5-oxopentanoate-2,2,3,3,4-D₅

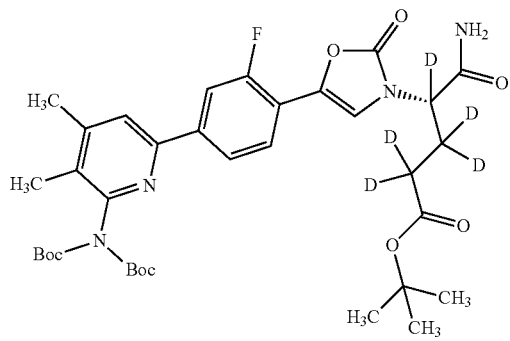

(2D)

To the solution of tert-butyl 5-amino-4-(5-(2-fluoro-4-(4,4,5,5-tetramethyl-1,3,2-dioxaborolan-2-yl)phenyl)-2-oxooxazol-3(2H)-yl)-5-oxopentanoate-2,2,3,3,4-D₅ (98 mg, 0.2 mmol) and tert-butyl (tert-butoxycarbonyl)(6-chloro-3,4-dimethylpyridin-2-yl) carbamate (67.2 mg, 0.19 mmol) in a mixture of dioxane (1.6 mL) and water (0.4 mL), were added K₃PO₄ (120 mg, 0.57 mmol) and XPhos Pd G2 (14.8 mg, 0.019 mmol). The reaction mixture was degassed under N₂ for 5 min. The reaction mixture was heated at 90° C. for 3 hours. After 3 hours, the reaction mixture was cooled to 0° C. The reaction was quenched with the addition of H₂O (1.8 mL). The reaction mixture was extracted with EtOAc, the organic layer was separated, dried over Na₂SO₄, filtered and concentrated to dryness to afford a black oil. The resulting crude product was purified by ISCO (12 g Silica gel), eluted with 100% Hex to 90% EtOAc/Hex. The product was eluted at 50-65% EtOAc/Hex. The combined product was concentrated to dryness and vacuum dried overnight to afford tert-butyl 5-amino-4-(5-(4-(6-(bis(tert-butoxycarbonyl)amino)-4,5-dimethylpyridin-2-yl)-2-fluorophenyl)-2-oxooxazol-3(2H)-yl)-5-oxopentanoate-2,2,3,3,4-D₅ as a yellow foam (90 mg, 69% yield). (Method C): retention time 1.106 min, [M+H]⁺690.1.

Example 2

To a solution of tert-butyl 5-amino-4-(5-(4-(6-(bis(tert-butoxycarbonyl)amino)-4,5-dimethylpyridin-2-yl)-2-fluorophenyl)-2-oxooxazol-3(2H)-yl)-5-oxopentanoate-2,2,3,3,4-D₅ (90 mg, 0.13 mmol) in anhydrous MeCN (2.1 mL) in a 10 mL-reactive vial, was added methanesulfonic acid (89 µL, 1.37 mmol). The reaction vial was sealed and heated at 70° C. for 7 h, followed by additional heating for 16 h. The reaction mixture was cooled to room temperature and additional methanesulfonic acid (76 µL) was added. The reaction mixture was heated at 70° C. for an additional 24 hours. The reaction mixture was cooled to room temperature, diluted with 0.6 mL MeCN, and purified by semi-prep HPLC. (HPLC conditions: Column: Luna C-18 (250×10 mm); Mobile phase A: 0.1% TFA in water; Mobile phase B: MeCN; Flow rate: 5 mL/min; Wavelength:220 nm; Gradient: 0 min: 10% B, 20 min: 60% B, 21 min: 95% B). The product eluted at 13-13.5 min. The fractions containing the product were combined and concentrated to remove all MeCN, then lyophilized overnight to afford 3-(5-(4-(6-amino-4,5-dimethylpyridin-2-yl)-2-fluorophenyl)-2-oxooxazol-3(2H)-yl)piperidine-2,6-dione-3,4,4,5,5-D₅ (32 mg, 53% yield). (Method C): retention time 0.783 min, [M+H]⁺ 415.7. ¹H NMR (400 MHz, DMSO-D₆) δ 11.15 (s, 1H), 7.91 (dd, 1H), 7.83 (m, 1H), 7.75 (m, 2H), 7.29 (s, 1H), 5.08 (s, 0.25H from partial D to H exchange), 2.35 (s, 3H), 2.12 (s, 3H).

Comparative Compound A 3-(2-oxo-5-phenyloxazol-3(2H)-yl)piperidine-2,6-dione

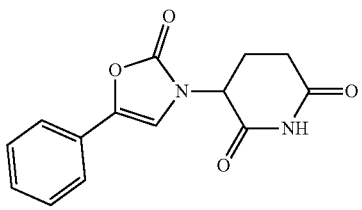 [SMILES: O=C1CCC(n2cc(-c3ccccc3)oc2=O)C(=O)N1]

3-(2-oxo-5-phenyloxazol-3(2H)-yl)piperidine-2,6-dione is disclosed as compound number I-33 in WO2019/060693 A1.

Preparation of Intermediate 3A: tert-butyl 5-amino-5-oxo-4-((2-oxo-2-phenylethyl)amino)pentanoate

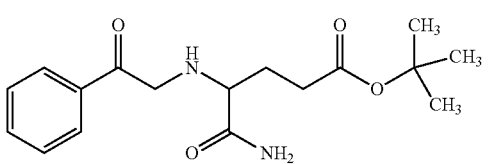

(3A)

To a stirred suspension of 2-bromo-1-phenylethan-1-one (200 mg, 1.0 mmol) and tert-butyl 4,5-diamino-5-oxopentanoate, HCl (360 mg, 1.5 mmol) in anhydrous acetonitrile (4.5 mL) was added sodium iodide (181 mg, 1.21 mmol) at 0° C. under argon. The reaction mixture was stirred for 5 min at the same temperature. DIPEA (351 µL, 2.01 mmol) was added drop wise to the reaction mixture. The reaction mixture was continued to stir at 0° C. for 2 h. The reaction mixture was warmed to room temperature and stirred overnight. The reaction was quenched with the addition of 10% sodium bisulfite solution. The mixture was extracted with DCM (3×10 mL). The combined organic phase was washed with water and brine, dried over anhydrous Na₂SO₄, filtered and concentrated under vacuo to afford tert-butyl 5-amino-5-oxo-4-((2-oxo-2-phenylethyl)amino)pentanoate (322 mg, crude). LCMS (Method A): retention time 1.215 min, [M+H]⁺ 321.1.

Preparation of Intermediate 3B: tert-butyl 5-amino-5-oxo-4-(2-oxo-5-phenyloxazol-3(2H)-yl)pentanoate

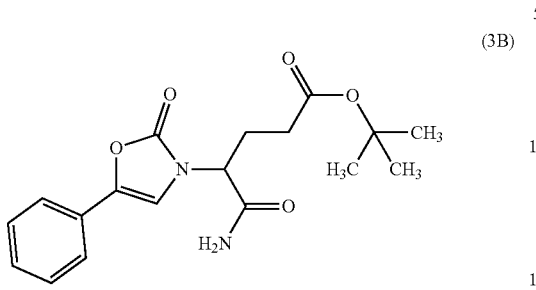

(3B)

To a stirred solution of tert-butyl 5-amino-5-oxo-4-((2-oxo-2-phenylethyl)amino) pentanoate (322 mg, 1.0 mmol) in anhydrous DMF (7 mL) were added CDI (407 mg, 2.5 mmol) and triethylamine (420 µL, 3.0 mmol) at 0° C. under argon. The reaction mixture was slowly warmed to room temperature and stirred overnight. The reaction was quenched with the addition of ice-cold water. The reaction mixture was extracted with EtOAc (3×15 mL). The combined organic phase was washed with water and brine solution, dried over anhydrous $Na_2SO_4$, filtered and concentrated under vacuo. The residue was purified by flash chromatography ($SiO_2$, 24 g column, 0-100% EtOAc/pet ether) to afford tert-butyl 5-amino-5-oxo-4-(2-oxo-5-phenyloxazol-3(2H)-yl)pentanoate (155 mg, 44%). LCMS (Method A): retention time 1.33 min, $[M+Na]^+$ 369.2; $^1H$ NMR (DMSO-$d_6$, 300 MHz) δ 7.75 (s, 2H), 7.5-7.6 (m, 2H), 7.42 (t, 2H, J=7.5 Hz), 7.3-7.4 (m, 2H), 4.50 (dd, 1H, J=4.3, 10.1 Hz), 2.2-2.3 (m, 3H), 2.0-2.1 (m, 1H), 1.38 (s, 9H).

Comparative Compound A

To a stirred solution of tert-butyl 5-amino-5-oxo-4-(2-oxo-5-phenyloxazol-3(2H)-yl)pentanoate (150 mg, 0.43 mmol) in acetonitrile (3.0 mL) was added methanesulfonic acid (42 µL, 0.65 mmol) at room temperature. The reaction mixture was heated at 90° C. for 1 h, cooled to room temperature, concentrated under vacuo and the residue was purified by reverse phase prep-HPLC (X-Bridge Phenyl C18 (250 mm*19 mm) 5 µm; mobile phase A: 10 mM ammonium acetate in water, mobile phase B: ACN; flow rate: 20.0 mL/min: gradient Time/% B: 0/30, 15/43, 15.1/100) to afford 3-(2-oxo-5-phenyloxazol-3(2H)-yl)piperidine-2,6-dione (25 mg, 21%) as a white solid. LCMS (Method A): retention time 1.582 min, $[M+H]^+$ 273.20; $^1H$ NMR (400 MHz, DMSO-$d_6$) δ=11.02 (br s, 1H), 7.70 (s, 1H), 7.52-7.47 (m, 2H), 7.47-7.42 (m, 2H), 7.35-7.30 (m, 1H), 5.03 (dd, J=5.3, 13.3 Hz, 1H), 2.95-2.84 (m, 1H), 2.68-2.60 (m, 1H), 2.48-2.35 (m, 1H), 2.21-2.11 (m, 1H).

Analytical LCMS conditions: Method A: ACQUITY UPLC® BEH C18 (3.0×50 mm) 1.7 µm; Mobile Phase A: 95:5 water:acetonitrile with 2.5 mM $NH_4O$ Ac; Mobile Phase B: 5:95 water:acetonitrile with 2.5 mM $NH_4OAc$; Temperature: 40° C.; Gradient: 20% B to 100% B over 2 min; flow: 0.7 mL/min; Detection: MS and UV (220 nm).

Method B: Column-Kinetex XB-C18 (75×3 mm-2.6 µm); Mobile Phase A: 10 mM $NH_4COOH$ in water: Mobile Phase B: Acetonitrile: Gradient: 20% B to 100% B over 4.6 min, Flow: 1.0 mL/min.

Comparative Compound B 3-(5-(4-bromo-2-fluorophenyl)-2-oxooxazol-3(2H)-yl)piperidine-2,6-dione

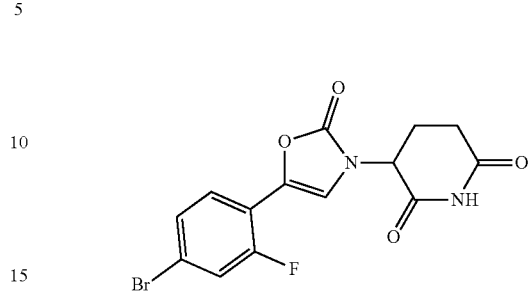

Preparation of Intermediate 4A: 3-(5-(4-bromo-2-fluorophenyl)-2-oxooxazol-3(2H)-yl)-1-(hydroxymethyl)piperidine-2,6-dione

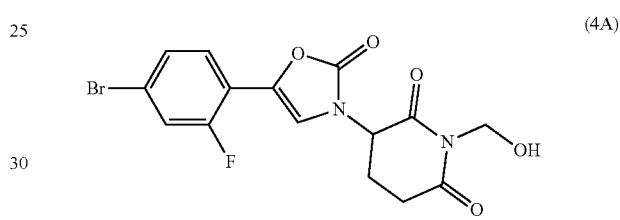

(4A)

To a stirred solution of 3-(5-(4-bromo-2-fluorophenyl)-2-oxooxazol-3(2H)-yl)-1-((2-(trimethylsilyl)ethoxy)methyl)piperidine-2,6-dione (200 mg, 0.4 mmol) in anhydrous DCM (2.0 mL) was added TFA (0.154 mL, 2.0 mmol) at mom temperature. The reaction mixture was stirred at room temperature for 2 h, concentrated under vacuo and the residue was co-evaporated with DME (4×) to afford 3-(5-(4-bromo-2-fluorophenyl)-2-oxooxazol-3(2H)-yl)-1-(hydroxymethyl)piperidine-2,6-dione (150 mg, 94%). LCMS (Method A): retention time 1.37 min, $[M+Na]^+$ 423.1.

Comparative Compound B

To a stirred solution of 3-(5-(4-bromo-2-fluorophenyl)-2-oxooxazol-3(2H)-yl)-1-(hydroxymethyl)piperidine-2,6-dione (180 mg, 0.45 mmol) in anhydrous DME (2255 µL) was added N,N'-dimethylethane-1,2-diamine (199 mg, 2.26 mmol) at 0° C. under nitrogen. The reaction mixture was warmed to room temperature and stirred for 30 min, cooled to 0° C., acidified with acetic acid (258 µL, 4.5 mmol) and then concentrated under vacuo (bath temp<30° C.). The residue was purified with reverse phase prep-HPLC (method: column: X-Bridge Phenyl (19 mm×250 mm*5 µm); mobile phase A: 10 mM ammonium acetate in water, mobile phase B: ACN; flow rate: 20 mL/min; gradient condition (Time/% B): 0/30, 14/51, 14.1/100) to afford 3-(5-(4-bromo-2-fluorophenyl)-2-oxooxazol-3(2H)-yl)piperidine-2,6-dione (67 mg, 40%). LCMS (Method A): retention time 2.155 min, $[M-H]^+$ 366.8; $^1H$ NMR (400 MHz, DMSO-$d_6$) δ=11.13 (br s, 1H), 7.75-7.70 (m, 1H), 7.66 (d, J=3.0 Hz, 1H), 7.53 (s, 1H), 7.52 (d, J=5.1 Hz, 1H), 5.06 (dd, J=5.3, 13.3 Hz, 1H), 2.94-2.80 (m, 1H), 2.70-2.54 (m, 2H), 2.16-2.08 (m, 1H).

Analytical LCMS Conditions

Method A: ACQUITY UPLC® BEH C18 (3.0×50 mm) 1.7 µm; Mobile Phase A: 95:5 water:acetonitrile with 2.5 mM $NH_4OAc$: Mobile Phase B: 5:95 water:acetonitrile with 2.5 mM $NH_4OAc$; Temperature: 40° C.; Gradient: 20% B to 100% B over 2 min; flow: 0.7 mL/min; Detection: MS and UV (220 nm).

Method B: Column-Kinetex XB-C18 (75×3 mm-2.6 µm): Mobile Phase A: 10 mM $NH_4COOH$ in water; Mobile Phase B: Acetonitrile; Gradient: 20% B to 100% B over 4.6 min, Flow: 1.0 mL/min.

Biological Assays

The pharmacological properties of the compounds of this invention may be confirmed by a number of biological assays. The exemplified biological assays, which follow, have been carried out with compounds of the invention.

Jurkat Cellular Degradation Assay

Jurkat cells were plated at 80,000 cells/well in 40 µL RPMI+10% FBS in a 384-well cell culture plate prior to using acoustic dispensing technology for adding a compound of interest. Cell cultures were incubated for 72 h at 37° C., and 5% $CO_2$. In order to facilitate analysis, cell cultures were spun down at 200 rpm for 5 min and the supernatant was discarded. After shaking the plate to dislodge the cell pellet, cells were resuspended in 50 qL of Fixation Buffer (eBioscience FoxP3 buffer set 00-5523-00) for 60 min at room temperature. After centrifuging and discarding the supernatant, cells were permeabilized with 50 µL of Permeabilization buffer (eBioscience FoxP3 buffer set 00-5523-00) for 10 min at room temperature. Following permeabilization, cells were spun down and the supernatant was replaced with 20 µL fluorescently labelled antibodies against Helios, Ikaros and Aiolos or corresponding Isotype controls in 1-Penneabilization buffer (Ikaros-Alexa488 [Biolegend, Cat #368408, 1:50], Helios-PE [CST, Cat #29360, 1:50], Aiolos-Alexa647 [Biolegend, Cat #371106 Biolegend, 1:25]) and staining reactions were incubated for 1 h at room temperature while protected from light. Subsequently, 30 µL of 1× Permeabilization buffer was added prior to centrifuging the cells and discarding the supernatant. Stained cells were resuspended in 25 µL of flow cytometry staining buffer [PBS+0.2% bovine serum albumin (BSA)] and analyzed using an Intellicyt Ique Plus flow cytometer.

TABLE A-1

Jurkat Cellular Degradation Assay: Maximum Observed Degradation

| Ex. No. | IKZF1 Ikaros max % deg. observed | IKZF2 Helios max % deg. observed | IKZF3 Aiolos max % deg. observed |
|---|---|---|---|
| 1 | 66% | 94% | 54% |
| Comparative Compound A | 57% | 27% | 46% |
| Comparative Compound B | 17% | 11% | 15% |

Table A-1 lists the maximum observed degradation of the IKZF1 protein, IKZF2 protein, and IKZF3 protein as measured in the Jurkat Cellular Degradation assay. The results in Table A-1 were rounded to two digits. In the Jurkat Cellular Degradation assay, a value of 100% indicated no detectable protein remaining or complete degradation of the protein; and a value of 0% indicated no detectable degradation of the protein by the test compound. In the study reported in Table A-1, Example 1 was observed to degrade greater than 90% of the IKZF2 (Helios) protein. In contrast, Comparative Compound A and Comparative Compound B were observed to degrade less than 30% of the IKZF2 protein.

TABLE A-2

Jurkat Cellular Degradation Assay: $DC_{50}$*

| Ex. No. | IKZF1 Ikaros $DC_{50}$ (nM) | IKZF2 Helios $DC_{50}$ (nM) | IKZF3 Aiolos $DC_{50}$ (nM) |
|---|---|---|---|
| 1 | 1,076 | 13.6 | 4,915 |
| Comparative Compound A | 1,520 | >10,000 | >10,000 |
| Comparative Compound B | >10,000 | >10,000 | >10,000 |

*$DC_{50}$ is defined as the concentration of compound required to reduce levels of a given protein by 50% compared to treatment with DMSO alone.

Human T Regulatory Cells Degradation Assay

Cryopreserved human T regulatory cells were thawed in RPMI+10% FBS+20 ng/mL IL-2. After being spun at 1200 rpm for 5 mins, the cells were resuspended in RPMI+10% FBS+20 ng/mL and rested at 37° C. with 5% $CO_2$ for 3 hours. The cells were then plated at 40,000 cells/well in 40 µL RPMI+10% FBS+20 ng/mL human IL-2 in a 384 well cell culture plate prior to using acoustic dispensing technology (ECHO 555) for adding compounds of interest. Cell cultures were incubated for 20 hours at 37° C., and 5% $CO_2$. In order to facilitate analysis, cell cultures were spun down at 1200 rpm for 5 minutes and the supernatant was discarded using an EL406 plate washer. After washing three times with 70 µL PBS, cell pellets were resuspended in 50 µL of near IR viability staining solution (Life Technologies, Cat #L34975) and incubated for 30 minutes on ice protected from light. Cells were washed three times with 70 pL PBS+0.5% BSA using an EL406 plate washer. After shaking the plate to dislodge the cell pellet, cells were resuspended in 50 µL of Fixation Buffer (eBioScience FoxP3 buffer set 00-5523-00) for 60 minutes at room temperature. After centrifuging and discarding the supernatant, cells were permeabilized with 50 µL of permeabilization buffer (eBioScience FoxP3 buffer set 00-5523-00) for 10 minutes at room temperature. Following permeabilization, cells were spun down and the supernatant was replaced with 30 µL fluorescently labelled antibodies against Helios in 1× Permeabilization buffer (Helios-APC [BioLegend, Cat #137222, 1:50]) and staining reactions were incubated for 1 hour at room temperature; protected from light. Subsequently, 30 µL of 1× Permeabilization buffer was added prior to centrifuging the cells and discarding the supernatant. Stained cells were resuspended in 30 µL of flow cytometry staining buffer (PBS+0.5% BSA) and analyzed using an Intellicyt Ique Plus flow cytometer.

TABLE B-1

Human T Regulatory Cells Degradation Assay: Maximum Observed Degradation

| Ex. No. | IKZF1 Ikaros max % deg. observed | IKZF2 Helios max % deg. observed |
|---|---|---|
| 1 | 55% | 99% |

Table B-1 lists the maximum observed degradation of the IKZF1 protein and IKZF2 protein as measured in the Human T Regulatory Cells Degradation assay. The results in Table B-1 were rounded to two digits. In the Human T Regulatory assay, a value of 100% indicated no detectable protein remaining or complete degradation of the protein; and a value of 0% indicated no detectable degradation of the protein by the test compound. In the study reported in Table B-1, Example 1 was observed to degrade 55% of the IKZF1 (Ikaros) protein.

TABLE B-2

Human T Regulatory Cells Degradation Assay: $DC_{50}$*

| Ex. No. | IKZF1 Ikaros $DC_{50}$ (nM) | IKZF2 Helios $DC_{50}$ (nM) |
|---|---|---|
| 1 | 5,466 | 5.2 |

*DC50 is defined as the concentration of compound required to reduce levels of a given protein by 50% compared to treatment with DMSO alone.

Human T Regulatory Cells Reprogramming Assay

Human $CD4^+$ T cells were isolated from fresh healthy leukopaks (Stemcell Technologies) using the RosetteSep Human $CD4^+$ T cell enrichment cocktail (Stemcell Technologies) and Ficoll density gradient centrifugation. Leukopaks were diluted with an equal volume of phosphate-buffered saline (PBS [Gibco]) supplemented with 2% fetal bovine serum (FBS, VWR Lifescience) and incubated with RosetteSep Human $CD4^+$ T cell enrichment cocktail for 20 minutes before layering on Ficoll-Paque Plus solution (GE Health Care). The cell-rich interface layer was harvested and washed twice with PBS supplemented with 2% FBS. Regulatory T cells were then isolated manually using the EasySep Human $CD4^+CD127^{low}CD25^+$ Regulatory T cell isolation kit (Stemcell Technologies) according to the manufacturer's instructions. Cells were rested overnight in Roswell Park Memorial Institute (RPMI) 1640 media (Gibco) supplemented with 10% FBS, Pen/Strep (Gibco), MEM-NEAA (Gibco), and sodium pyruvate (Gibco) in a humidified incubator (37° C., 5% $CO_2$). Cells were then stained for CD4 (clone: RPA-T4, Biolegend), CD25 (clone: 2A3, BD Biosciences), and CD127 (clone: hIL-7R-M21, BD Biosciences). $CD4^+CD127^{low}CD25^+$ cells were sorted on a BD FACS Aria Fusion sorter. Sorted cells were immediately used or cryopreserved for downstream assays.

Fresh or cryopreserved flow sorted $CD4^+CD127^{low}CD25^+$ Treg cells were cultured at 25,000-50,000 cells/well of 96-well round bottom plates in RPMI 1640 media (Gibco) supplemented with 10% FBS, Pen/Strep (Gibco), MEM-NEAA (Gibco), and sodium pyruvate (Gibco). Cells were stimulated with Treg Xpander beads (Thermo Fisher) at cells-to-beads ratio of 1:4 in the presence of 500 U/mL recombinant human IL-2 (Proleukin). Compounds were added at titrated doses and cells were incubated at 37° C., 5% $CO_2$ for 12-13 days. Recombinant human IL-2 and compound were replenished every 2-3 days during the entire culture duration. On day 12 or 13, cells were restimulated with phorbol 12-myristate 13-acetate (PMA) and ionomycin before proceeding with flow cytometry staining and analysis.

For flow cytometry staining, cells were washed twice with flow cytometry staining buffer (Thermo Fisher) and incubated in Human Tru-stain Fc block (Biolegend) for 10 minutes before adding eFluor780 viability dye (Thermo Fisher) and surface marker antibody cocktail for 30 minutes at 4° C. Cells were then fixed and permeabilized by incubation with FoxP3 transcription factor staining buffer (Thermo Fisher) for 30 minutes at 4° C., as per the kit manufacturer's instructions. Cells were washed twice with the Perm/Wash buffer suppled in the kit as per the manufacturer's instructions and incubated overnight at 4° C. with an intracellular antibody cocktail comprised of antibodies specific for the transcription factors shown in Table C. Cells were washed twice with Perm/Wash buffer and resuspended in flow cytometry staining buffer (Thermo Fisher) prior to acquisition. Sample acquisition and analysis was performed using a BD LSRFortessa (BD Biosciences) flow cytometer. Single stain controls for each fluorochrome were prepared using UltraComp eBead Compensation Beads (Thermo Fisher). Data were analyzed using FlowJo version 10 and GraphPad Prism Software.

TABLE C

Antibodies Used for Flow Sorting and Analysis

| Marker | Fluorochrome |
|---|---|
| Viability | eFluor780 |
| CD3 | BUV395 |
| CD4 | BUV805 |
| CD8 | FITC |
| CD25 | BV606 |
| FoxP3 | BV421 |
| HELIOS | PE-Cy7 |
| EOS | PE |

TABLE C-1

Human T Regulatory Cell Reprogramming Assay-Maximum Observed Degradation

| Ex. No. | IKZF2 Helios max % deg. observed | IKZF4 Eos max % deg. observed |
|---|---|---|
| 1 | 83% | 73% |
| 2 | 88% | 96% |
| Comparative Compound A | 1% | 0% |
| Comparative Compound B | 6% | 11% |

Table C-1 lists the maximum observed degradation of the IKZF2 protein and IKZF4 protein as measured in the Human T Regulatory Cells Reprogramming assay. The results in Table C-1 were rounded to two digits. In the Human T Regulatory Cells Reprogramming assay, a value of 100% indicated no detectable protein remaining or complete degradation of the protein; and a value of 0% indicated no detectable degradation of the protein by the test compound. In the study reported in Table D-1, Examples 1 and 2 reduced the level of the IKZF2 (Helios) protein by at least 83% and the level of the IKZF4 (Eos) protein by at least 73%. In contrast, Comparative Compound A and Comparative Compound B decreased the level of the IKZF2 (Helios) protein by 6% or less; and decreased the level of IKZF4 (Eos) protein by 11% or less.

TABLE C-2

Human T Regulatory Cell Reprogramming Assay: $DC_{50}$*

| Ex. No. | IKZF2 Helios $DC_{50}$ (nM) | IKZF4 Eos $DC_{50}$ (nM) |
|---|---|---|
| 1 | 85 | 1.5 |
| 2 | 42 | 0.63 |

TABLE C-2-continued

Human T Regulatory Cell Reprogramming Assay: $DC_{50}$*

| Ex. No. | IKZF2 Helios $DC_{50}$ (nM) | IKZF4 Eos $DC_{50}$ (nM) |
| --- | --- | --- |
| Comparative Compound A | >1000 | >1000 |
| Comparative Compound B | >1000 | >1000 |

*$DC_{50}$ is defined as the concentration of compound required to reduce levels of a given protein by 50% compared to treatment with DMSO alone.

Human CD8+ T Cell Degradation Assay

Cryopreserved healthy donor human peripheral blood mononuclear cells (PBMC; obtained from Stemcell Technologies or Blood Works Northwest) from two healthy donors were thawed and seeded at 500,000 cells/well of 96-well round bottom plates in RPMI 1640 media (Gibco) supplemented with 10% FBS, Pen/Strep (Gibco), MEM-NEAA (Gibco), and sodium pyruvate (Gibco). Cells were treated with titrated doses of compound for 24 hours at 37° C., 5% $CO_2$ before analyzing by flow cytometry.

For flow cytometry staining, cells were washed twice with flow cytometry staining buffer (Thermo Fisher) and incubated in Human Tru-stain Fc block (Biolegend) for 10 minutes before adding eFluor780 viability dye (Thermo Fisher) and surface marker antibody cocktail containing LD-eFluor780, CD3-BUV-395, CD4-BUV805, CD8-FITC, CD25-BV605, FoxP3-BV421, HELIOS-PE-Cy7, EOS-PE, IKAROS-PECF594, AIOLOS-AF647 for 30 minutes at 4° C. Cells were then fixed and permeabilized by incubation with permeabilization buffer (eBioscience FoxP3 buffer set 00-5523-00) for 30 minutes at 4° C., as per the kit manufacturer's instructions. Cells were washed twice with the Perm/Wash buffer suppled in the kit as per the manufacturer's instructions and incubated overnight at 4° C. with an intracellular antibody cocktail comprised of antibodies specific for the transcription factors shown in Table C. Cells were washed twice with Perm/Wash buffer and resuspended in flow cytometry staining buffer (Thermo Fisher) prior to acquisition. Sample acquisition and analysis was performed using a BD LSRFortessa (BD Biosciences) flow cytometer. Single stain controls for each fluorochrome were prepared using UltraComp eBead Compensation Beads (Thermo Fisher). Data were analyzed using FlowJo version 10 and GraphPad Prism Software.

TABLE D-1

Human CD8+ T Cell Reprogramming Assay-Maximum Observed Degradation

| Ex. No. | IKZF1 Ikaros | IKZF3 Aiolos |
| --- | --- | --- |
| 1 | 74% | 77% |
| 2 | 66% | 71% |
| Comparative Compound A | 74% | 80% |
| Comparative Compound B | 17% | 0% |

TABLE D-2

Human CD8+ T Cell Reprogramming Assay: $DC_{50}$*

| Ex. No. | IKZF1 Ikaros $DC_{50}$ (nM) | IKZF3 Aiolos $DC_{50}$ (nM) |
| --- | --- | --- |
| 1 | 102 | 19 |
| 2 | 139 | 26 |
| Comparative Compound A | 113 | 21 |
| Comparative Compound B | >1000 | >1000 |

*$DC_{50}$ is defined as the concentration of compound required to reduce levels of a given protein by 50% compared to treatment with DMSO alone.

Table D-1 lists the maximum observed degradation of the IKZF1 protein and IKZF3 protein as measured in the Human CD8+ T Cell Reprogramming assay. The results in Table D-1 were rounded to two digits. In the Human CD8+ T Cell Reprogramming assay, a value of 100% indicated no detectable protein remaining or complete degradation of the protein; and a value of 0% indicated no detectable degradation of the protein by the test compound.

TABLE E

Maximum Observed Degradation of IKZF1-4: Comparison of Examples 1-2 and Comparative Compounds A and B*

| Ex. No. | IKZF1** Ikaros max % deg. observed | IKZF2*** Helios max % deg. observed | IKZF3** Aiolos max % deg. observed | IKZF4*** Eos max % deg. observed |
| --- | --- | --- | --- | --- |
| 1 | 74% | 83% | 77% | 73% |
| 2 | 66% | 88% | 71% | 96% |
| Comparative Compound A | 74% | 1% | 80% | 0% |
| Comparative Compound B | 17% | 6% | 0% | 11% |

*All data reported as an average of values where N > 1.
**IKZF1 and IKZF3: Human CD8+ T Cell Reprogramming Assay (Table D-1)
***IKZF2 and IKZF4: Human T Regulatory Cell Reprogramming Assay (Table C-1)

Examples 1 and 2 have been compared to Comparative Compound A disclosed in WO2019/060693 A1 and Comparative Compound B, and have been found to be especially advantageous. Examples 1 and 2 have the surprising advantage of decreasing the levels of the four IKZF1-4 proteins Ikaros, Helios. Aiolos, and Eos. As shown in Tables C-1 and D-1 in the reported tests: (i) Examples 1 and 2 decreased the level of IKZF1 (Ikaros) by 74% and 66%, respectively (Table D-1): (ii) Examples 1 and 2 decreased the level of the IKZF2 (Helios) protein by 83% and 88/a, respectively (Table C-1); (iii) Examples 1 and 2 decreased the level of IKZF3 (Aiolos) by 77% and 71%, respectively (Table D-1); and (iv) Examples 1 and 2 decreased the level of IKZF4 (Eos) by 73% and 96%, respectively (Table C-1). In contrast, in similar tests, Comparative Compound A and Comparative Compound B decreased the level of the IKZF2 (Helios) protein (Table C-1) by 6% or less; and decreased the level of IKZF4 (Eos) protein (Table C-1) by 11% or less.

The present invention fills the foregoing need by providing compounds that are useful to decrease the levels of the four IKZF1-4 proteins Ikaros, Helios. Aiolos, and Eos.

What is claimed is:

1. A compound having the structure:

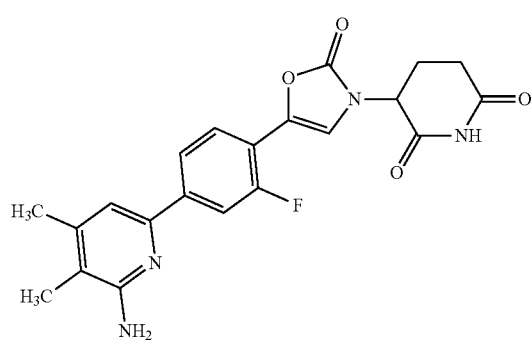 [SMILES: Cc1cc(-c2ccc(-c3cn(C4CCC(=O)NC4=O)c(=O)o3)c(F)c2)nc(N)c1C]

or stereoisomers, tautomers, or salts thereof.

2. A compound having the structure:

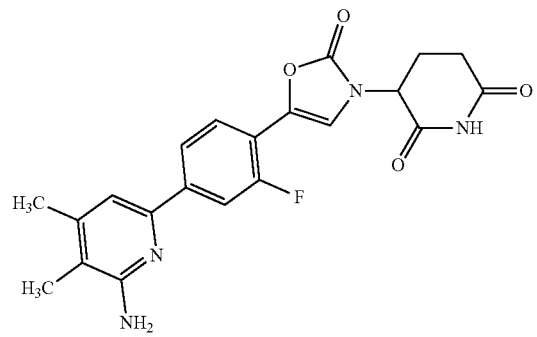 [SMILES: Cc1cc(-c2ccc(-c3cn(C4CCC(=O)NC4=O)c(=O)o3)c(F)c2)nc(N)c1C]

or stereoisomers or tautomers thereof.

3. A salt of a compound having the structure:

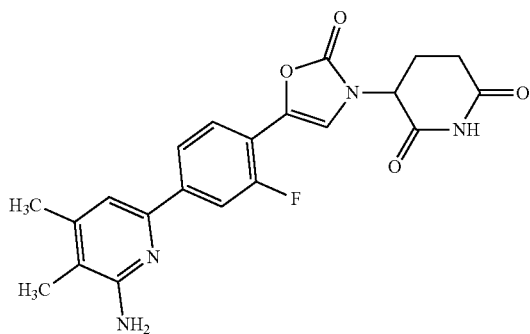 [SMILES: Cc1cc(-c2ccc(-c3cn(C4CCC(=O)NC4=O)c(=O)o3)c(F)c2)nc(N)c1C]

or stereoisomers or tautomers thereof.

4. The compound according to claim 1, wherein said compound is:
- (S)-3-(5-(4-(6-amino-4,5-dimethylpyridin-2-yl)-2-fluorophenyl)-2-oxooxazol-3 (2H)-yl) piperidine-2,6-dione; or
- (R)-3-(5-(4-(6-amino-4,5-dimethylpyridin-2-yl)-2-fluorophenyl)-2-oxooxazol-3 (2H)-yl) piperidine-2,6-dione;

or tautomers or salts thereof.

5. A compound selected from:

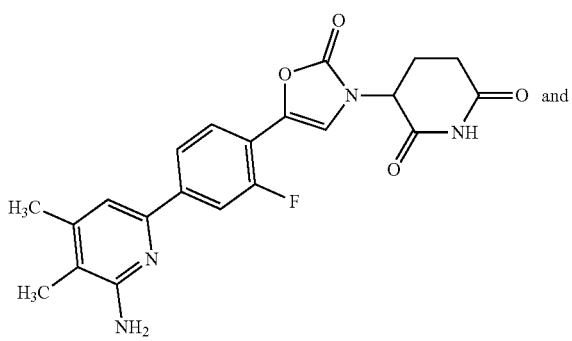

and

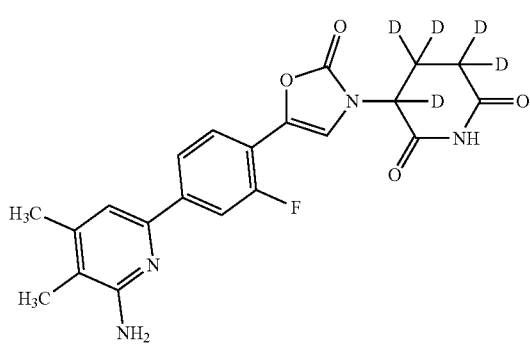

or stereoisomers, tautomers, or salts thereof.

6. The compound according to claim 5 having the structure:

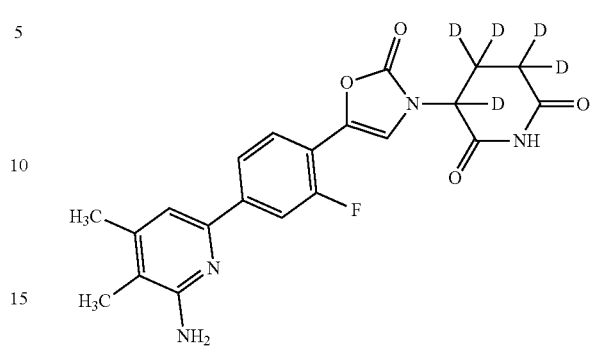

or stereoisomers, tautomers, or salts thereof.

7. The compound according to claim 6 or stereoisomers or tautomers thereof.

8. The salt of a compound according to claim 6 or stereoisomers or tautomers thereof.

9. The compound according to claim 6, wherein said compound is:
- (S)-3-(5-(4-(6-amino-4,5-dimethylpyridin-2-yl)-2-fluorophenyl)-2-oxooxazol-3 (2H)-yl) piperidine-2,6-dione-3,4,4,5,5-d5; or
- (R)-3-(5-(4-(6-amino-4,5-dimethylpyridin-2-yl)-2-fluorophenyl)-2-oxooxazol-3 (2H)-yl) piperidine-2,6-dione-3,4,4,5,5-d5;

or tautomers or salts thereof.

10. A pharmaceutical composition comprising a compound according to claim 1 or stereoisomers, tautomers, or a pharmaceutically acceptable salt thereof; and a pharmaceutically acceptable carrier.

11. A pharmaceutical composition comprising a compound according to claim 2, or stereoisomers or tautomers thereof; and a pharmaceutically acceptable carrier.

12. A pharmaceutical composition comprising a pharmaceutical salt of the compound according to claim 3, or stereoisomers or tautomers thereof; and a pharmaceutically acceptable carrier.

13. A pharmaceutical composition comprising a compound according to claim 6, or stereoisomers, tautomers, or a pharmaceutically acceptable salt thereof; and a pharmaceutically acceptable carrier.

14. A pharmaceutical composition comprising a compound according to claim 7, or stereoisomers or tautomers thereof; and a pharmaceutically acceptable carrier.

15. A pharmaceutical composition comprising a pharmaceutically acceptable salt of the compound according to claim 8, or stereoisomers or tautomers thereof; and a pharmaceutically acceptable carrier.

16. A method for the treatment of cancer, in a patient comprising administering to said patient a therapeutically effective amount of a compound according to claim 1, or stereoisomers, tautomers thereof, or a pharmaceutically acceptable salt thereof, wherein said cancer is selected from cancer of the colon, gastric, pancreatic cancer, breast cancer, prostate cancer, lung cancer, ovarian cancer, cervical cancer, renal cancer, cancer of the head and neck, lymphoma, leukemia, multiple myeloma, and melanoma.

17. The method according to claim 16, wherein said cancer is selected from cancer of the colon, gastric, pancreatic cancer, breast cancer, prostate cancer, lung cancer, ovarian cancer, cervical cancer, renal cancer, cancer of the head and neck, and melanoma.

18. The method according to claim 16 in combination with a second agent, wherein said second agent is selected from an antagonist of PD1/PD-L1 axis, an antagonist of CTLA4, an antagonistic LAG-3, a chemotherapeutic agent, radiation, or an anti-tumor vaccine.

19. A method for the treatment of cancer, in a patient comprising administering to said patient a therapeutically effective amount of a compound according to claim 2, or stereoisomers or tautomers thereof, wherein said cancer is selected from cancer of the colon, gastric, pancreatic cancer, breast cancer, prostate cancer, lung cancer, ovarian cancer, cervical cancer, renal cancer, cancer of the head and neck, lymphoma, leukemia, multiple myeloma, and melanoma.

20. The method according to claim 19, wherein said cancer is selected from cancer of the colon, gastric, pancreatic cancer, breast cancer, prostate cancer, lung cancer, ovarian cancer, cervical cancer, renal cancer, cancer of the head and neck, and melanoma.

21. The method according to claim 19 in combination with a second agent, wherein said second agent is selected from an antagonist of PD1/PD-L1 axis, an antagonist of CTLA4, an antagonistic LAG-3, a chemotherapeutic agent, radiation, or an anti-tumor vaccine.

22. A method for the treatment of cancer, in a patient comprising administering to said patient a therapeutically effective amount of a pharmaceutically acceptable salt of compound according to claim 3, or stereoisomers or tautomers thereof, wherein said cancer is selected from cancer of the colon, gastric, pancreatic cancer, breast cancer, prostate cancer, lung cancer, ovarian cancer, cervical cancer, renal cancer, cancer of the head and neck, lymphoma, leukemia, multiple myeloma, and melanoma.

23. The method according to claim 22, wherein said cancer is selected from cancer of the colon, gastric, pancreatic cancer, breast cancer, prostate cancer, lung cancer, ovarian cancer, cervical cancer, renal cancer, cancer of the head and neck, and melanoma.

24. The method according to claim 22 in combination with a second agent, wherein said second agent is selected from an antagonist of PD1/PD-L1 axis, an antagonist of CTLA4, an antagonistic LAG-3, a chemotherapeutic agent, radiation, or an anti-tumor vaccine.

25. A method for the treatment of cancer, in a patient comprising administering to said patient a therapeutically effective amount of a compound according to claim 6, or stereoisomers, tautomers, or a pharmaceutically acceptable salt thereof, wherein said cancer is selected from cancer of the colon, gastric, pancreatic cancer, breast cancer, prostate cancer, lung cancer, ovarian cancer, cervical cancer, renal cancer, cancer of the head and neck, lymphoma, leukemia, multiple myeloma, and melanoma.

26. The method according to claim 25, wherein said cancer is selected from cancer of the colon, gastric, pancreatic cancer, breast cancer, prostate cancer, lung cancer, ovarian cancer, cervical cancer, renal cancer, cancer of the head and neck, and melanoma.

27. The method according to claim 25 in combination with a second agent, wherein said second agent is selected from an antagonist of PD1/PD-L1 axis, an antagonist of CTLA4, an antagonistic LAG-3, a chemotherapeutic agent, radiation, or an anti-tumor vaccine.

\* \* \* \* \*